US012678124B2

(12) United States Patent
Li et al.

(10) Patent No.:  US 12,678,124 B2
(45) Date of Patent:    Jul. 14, 2026

(54) METHOD AND APPARATUS WITH USER GUIDANCE AND AUTOMATED IMAGE SETTING SELECTION FOR MITRAL REGURGITATION EVALUATION

(71) Applicant: KONINKLIJKE PHILIPS N.V., Eindhoven (NL)

(72) Inventors: Qianxi Li, Cambridge, MA (US); Claudia Errico, Medford, MA (US); Hua Xie, Cambridge, MA (US); Ramon Quido Erkamp, Swampscott, MA (US); Benoit Mory, Medford, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 291 days.

(21) Appl. No.: 18/285,028

(22) PCT Filed: Mar. 24, 2022

(86) PCT No.: PCT/EP2022/057819
§ 371 (c)(1),
(2) Date: Sep. 29, 2023

(87) PCT Pub. No.: WO2022/207463
PCT Pub. Date: Oct. 6, 2022

(65) Prior Publication Data
US 2024/0173007 A1     May 30, 2024

Related U.S. Application Data

(60) Provisional application No. 63/168,493, filed on Mar. 31, 2021.

(51) Int. Cl.
*A61B 8/00*        (2006.01)
*A61B 8/06*        (2006.01)
(Continued)

(52) U.S. Cl.
CPC ................. *A61B 8/06* (2013.01); *A61B 8/42* (2013.01); *A61B 8/463* (2013.01); *A61B 8/469* (2013.01);
(Continued)

(58) Field of Classification Search
CPC ......... A61B 8/06; A61B 8/065; A61B 8/0883; A61B 8/42; A61B 8/4245; A61B 8/463;
(Continued)

(56) References Cited

U.S. PATENT DOCUMENTS

2013/0345563 A1* 12/2013 Stuebe ................... A61B 5/316
                                                                          600/440
2014/0052001 A1     2/2014 Ionasec et al.
(Continued)

FOREIGN PATENT DOCUMENTS

WO         2019197427 A1    10/2019
WO     WO-2020020770 A1 *  1/2020  ............. A61B 8/585

OTHER PUBLICATIONS

Chew, PG et al. "Multimodality imaging for the quantitative assessment of mitral regurgitation", Quant Imaging Med Surg 2018;8(3):342-359 (Year: 2018).*
(Continued)

*Primary Examiner* — Keith M Raymond
*Assistant Examiner* — Milton Truong

(57)              ABSTRACT

Ultrasound imaging system and method for improving MR quantification is described. An ultrasound imaging system according to some embodiments may be programmed to execute one or more routines and use one or more trained predictive models to provide user guidance and/or automation for positioning the ultrasound probe to acquire a desired cardiac view and tune the imaging settings of the system for each measurement of the MR quantification process.

15 Claims, 13 Drawing Sheets

(51) Int. Cl.
  *G06T 7/00* (2017.01)
  *G16H 40/63* (2018.01)
(52) U.S. Cl.
  CPC ............... *A61B 8/488* (2013.01); *A61B 8/58* (2013.01); *G06T 7/0012* (2013.01); *G16H 40/63* (2018.01); *G06T 2200/24* (2013.01); *G06T 2207/10024* (2013.01); *G06T 2207/10132* (2013.01); *G06T 2207/20084* (2013.01); *G06T 2207/20092* (2013.01); *G06T 2207/30048* (2013.01)
(58) Field of Classification Search
  CPC ....... A61B 8/469; A61B 8/488; A61B 8/5223; A61B 8/58; G06T 2200/24; G06T 2207/10024; G06T 2207/10132; G06T 2207/20084; G06T 2207/20092; G06T 2207/30048; G06T 7/0012; G16H 40/63
  See application file for complete search history.

(56) References Cited

U.S. PATENT DOCUMENTS

| | | | |
|---|---|---|---|
| 2015/0272546 A1* | 10/2015 | Cheon | G16H 50/30 600/440 |
| 2015/0327838 A1 | 11/2015 | Francis et al. | |
| 2018/0103912 A1 | 4/2018 | Canfield et al. | |
| 2021/0174496 A1* | 6/2021 | Annangi | A61B 8/5223 |

OTHER PUBLICATIONS

Moraldo, M, et al. "A novel fully automated method for mitral regurgitant orifice area quantification" International Journal of Cardiology 166 (2013) 688-695 (Year: 2013).*

Heinle, Sheila, et al. "Comparison of Vena Contracta Width by Multiplane Transesophageal Echocardiography With Quantitative Doppler Assessment of Mitral Regurgitation", Am J Cardiol 1998;81:175-179 (Year: 1998).*

Wahlang, I. et al. "Deep Learning Methods for Classification of Certain Abnormalities in Echocardiography" Electronics 2021, 10, 495 (Year: 2021).*

International Search Report and Written Opinion for PCT/EP2022/057819; Mailing date: Aug. 4, 2022, 10 pages.

Moraldo, M. et al., "A novel fully automated method for mitral regurgitant orifice area quantification", Int J Cardiol., 2013 vol. 166, Issue 3, pp. 688-695.

Li, C-H. et al., "Role of Imaging Techniques in Percutaneous Treatment of Mitral Regurgitation", Rev Esp Cardiol (Engl Ed), 2016, vol. 69, No. 4, pp. 421-436.

Lloyd-Jones, D. et al., "Heart disease and stroke statistics—2010 update: a report from the American Heart Association", Circulation, 2010, vol. 121, Issue 7, pp. e46-e215.

Nkomo, V. et al., "Burden of valvular heart diseases: a population-based study", The Lancet, 2006, vol. 368, Issue 9540, pp. 1005-1011.

Ancona, R. et al., "Mitral valve incompetence: epidemiology and causes", 2018, vol. 16, No. 11, 9 pages.

Trochu, J-N. et al., "Mitral regurgitation—Unmet need for improved management strategies", Int J Cardiol Heart Vasc., 2014, vol. 5, pp. 26-41.

Grigioni, F. et al., "Outcomes in Mitral Regurgitation Due to Flail Leaflets: A Multicenter European Study", JACC: Cardiovascular Imaging, 2008, vol. 1, Issue 2, pp. 133-141.

Enriquez-Sarano, M. et al., "Quantitative Determinants of the Outcome of Asymptomatic Mitral Regurgitation", N Engl J Med., 2005, vol. 352, pp. 875-883.

MitraClip, "Mitral Regurgitation (MR) is Prevalent and Growing", retrieved from https://mitraclip.com/physician/mitral-regurgitation-prevalence, 2022, 9 pages.

O'Gara, P. et al., "2017 ACC Expert Consensus Decision Pathway on the Management of Mitral Regurgitation: A Report of the American College of Cardiology Task Force on Expert Consensus Decision Pathways", Journal of the American College of Cardiology, 2017, vol. 70, Issue 19, pp. 2421-2449.

Chew, P. et al., "Multimodality imaging for the quantitative assessment of mitral regurgitation", Quant Imaging Med Surg., 2018, vol. 8, Issue 3,pp. 342-359.

Nishimura, R. et al., "2017 AHA/ACC Focused Update of the 2014 AHA/ACC Guideline for the Management of Patients With Valvular Heart Disease: A Report of the American College of Cardiology/American Heart Association Task Force on Clinical Practice Guidelines", Circulation, 2017, vol. 135, Issue 25, pp. e1159-e1195.

Zoghbi, W. et al., "Recommendations for evaluation of the severity of native valvular regurgitation with two-dimensional and Doppler echocardiography", J Am Soc Echocardiogr., 2003, vol. 16, Issue 7, pp. 777-802.

Thavendiranathan, P. et al., "Quantitative Assessment of Mitral Regurgitation: How Best to Do It", JACC: Cardiovascular Imaging, 2012, vol. 5, Issue 11, pp. 1161-1175.

123 Sonography, "12.7 Quantification of mitral regurgitation", retrieved from https://123sonography.com/ebook/quantification-of-mitral-regurgitation, 2023, 14 Pages.

Lambert, A.S., "Proximal isovelocity surface area should be routinely measured in evaluating mitral regurgitation: a core review", Anesth Analg, 2007, vol. 105, Issue 4, pp. 940-943.

Thomas, N. et al., "Intraobserver variability in grading severity of repeated identical cases of mitral regurgitation", Am Heart Journal, 2008, vol. 156, Issue 6, pp. 1089-1094.

Pavliuk, V., "Echocardiographic Assesment of Mitral Regurgitation", retrieved from https://www.youtube.com/watch?v=O0EapRNaNJ0, 2013, 27 minutes.

Cape, E. et al., "Increased heart rate can cause underestimation of regurgitant jet size by Doppler color flow mapping", Journal of the American College of Cardiology, 1993, vol. 21, Issue 4, pp. 1029-1037.

123 Sonography, "Jet Direction and the Mechanism of Mitral Regurgitation", retrieved from https://www.youtube.com/watch?v=nBHZZXDAzO4, 2010, 2 minutes.

Stewart, W. et al., "Evaluation of mitral leaflet motion by echocardiography and jet direction by doppler color flow mapping to determine the mechanism of mitral regurgitation", Journal of the American College of Cardiology, 1992, vol. 20, Issue 6, pp. 1353-1361.

Nkomo, V. et al., "Chronic primary mitral regurgitation: General management", retrieved from hhttps://medilib.ir/uptodate/show/8132, 2023, 7 pages.

Krizhevsky, A. et al., "ImageNet Classification with Deep Convolutional Neural Networks", NIPS 2012, 9 pages.

* cited by examiner

300

310

Display MR Exam GUI

312

Receive at least one of measurement selection and automation mode selection

314

Display live cardiac images

316

Provide positioning guidance as live images are displayed

318

Acoustic setting optimization

320

Record a sequence of images with MR specific settings

322

Extract target frame for selected measurement

324

Obtain selected measurement

326

Return to main MR Exam GUI GUI and select another measurement

METHOD AND APPARATUS WITH USER GUIDANCE AND AUTOMATED IMAGE SETTING SELECTION FOR MITRAL REGURGITATION EVALUATION

This application is the U.S. National Phase application under 35 U.S.C. § 371 of International Application No. PCT/EP2022/057819, filed on Mar. 24, 2022, which claims the benefit of European Application 63/168,493, filed Mar. 31, 2021. These applications are hereby incorporated by reference herein.

FIELD OF THE INVENTION

The present disclosure relates generally to ultrasound imaging and, in particular, to a method and system that provides user guidance and automated imaging setting selection for improved mitral regurgitation evaluation.

BACKGROUND OF THE INVENTION

Various studies have concluded that mitral regurgitation (MR) is the most frequent valvular heart disease in the United States, with nearly 1 in 10 people age 74 and older having moderate or severe MR. It has also been found that MR is the second most frequent indication for valve surgery in Europe. Also, the number of MR patients continues to increase due to the dramatic increase in life expectancy that began in the last half of the 20th century. MR is characterized by the retrograde flow of blood from the left ventricle (LV) into the left atrium (LA) during the systolic phase of the cardiac cycle. It is a progressive disease which leads to a cascade of events ultimately leading to LV failure, pulmonary hypertension, atrial fibrillation, heart failure, then death, if left untreated. It has been found that the one-year mortality rate of MR can be up to 57%.

The most commonly used imaging modality for assessing MR is echocardiography (or echo), and more specifically transthoracic echocardiography (TTE), with Doppler color flow applied. Advances in 3D TTE imaging for MR evaluation has further improved the prognostic power of echo exams. Apart from echo, cardiovascular magnetic resonance (CMR) has also been increasingly used for MR quantification. Other techniques such as exercise echocardiography (i.e. stress echo), tissue Doppler imaging and speckle-tracking echocardiography can further offer complementary information on prognosis, with Doppler echo still being the mainstay for diagnosing MR.

MR management is challenging due to the variations in the causes and severity stages of MR and the corresponding treatment plans. Based on the etiology, MR can be classified into primary and secondary MR. Primary MR is caused by the defect or structural abnormalities of the valve apparatus components. Secondary MR, also known as functional MR, is associated LV dysfunction due to coronary heart disease (CHD) or (non-ischemic) cardiomyopathy, in which case the mitral valve leaflets are normal. The abnormal and dilated left ventricle causes papillary muscle displacement, which in turn results in leaflet tethering with associated annular dilation that prevents adequate leaflet coaptation. There are instances when both primary and secondary MR are present, which is referred to as mixed MR. It is recognized that primary and secondary MR are different diseases with different outcomes and indications for treatment. Treatment planning depends on proper identification of the etiology MR, accurate evaluation of diseases severity level/stage, coupled by awareness of the symptom and other clinical findings. Thus, determining the severity of MR is an important factor in MR management as it carries significant prognostic implications and determines the treatment strategies as well as the timing for surgical intervention if needed. Currently, accurate measurements and thus accurate diagnosis is operator dependent and thus systems and methods with user guidance and/or automated setting selection capabilities that can assist operators in obtaining accurate measurements, with repeatability, may be desirable.

SUMMARY OF THE INVENTION

While existing ultrasound imaging has proved useful for clinical guidance and diagnosis, there remains a need for improved systems and techniques that aid the operator (e.g. sonographer) in obtaining accurate measurements, specifically in the case of MR evaluations. Accurate classification of MR severity depends on accurate quantification of related clinical parameters, which can be imaged with ultrasound, but the imaging of which is challenging. Specifically, the cardiac landmarks typically used for MR quantification are: vena contracta width (VCW), regurgitant volume (RVol) and regurgitant fraction (RF), and effective regurgitant orifice area (EROA). However, these cardiac features are not easy to image. For example, the VCW, which is the narrowest portion of a jet that occurs at or just downstream from the orfice (see e.g., FIG. 1), is dynamic—that is, its size changes during a cardiac cycle. Also, the VCW is small (usually under 10 mm) and thus even small errors (on the order of 2 mm) can be significant, leading to a larger percentage error and misclassification of the regurgitation severity. RVol is calculated by subtracting the right ventricle (RV) stroke volume from the left ventricle (LV) across the left ventricular outflow tract (LVOT). The regurgitation fraction is measured as the ratio between mitral valve (MV) regurgitation volume to the RV stroke volume. EROA measures the area of the coaptation defect in the mitral valve. While ultrasound imaging guidelines for imaging these cardiac features are available, obtaining accurate measurements typically require a skilled operator, making the MR evaluation process error-prone and operator dependent. Embodiments of the present disclosure provide imaging methods and systems with embedded operator assistance for improving the MR evaluation process.

An imaging system according to some embodiments includes an ultrasound imaging device having a probe configured to transmit ultrasound into a subject (e.g., a patient) in accordance with acquisition settings and to receive ultrasound echoes for generating ultrasound images of the heart. The system further includes a user interface for controlling operations of the ultrasound imaging device, the user interface including a display for displaying the ultrasound images of the heart. The system includes a processor configured to provide (e.g., on a touch screen display) a graphical user interface (GUI) for an MR exam, the GUI being configured to enable the user to selectively activate automation settings (e.g., auto-TSP mode, auto-measure mode) and/or to select from a plurality of predetermined measurements consisting of vena contracta width (VCW), regurgitant volume (RVol) and regurgitant fraction (RF), and effective regurgitant orifice area (EROA), responsive to each of which the system displays a sequence of interface screens to assist the user with obtaining the selected measurements. The processor is configured, for one or more of the selected measurements of the plurality of measurements, to provide measurement-specific user guidance on the display for at least one of positioning the probe, adjusting acquisition settings, and determining a target frame from a sequence of ultrasound images for obtaining the selected measurement.

In some embodiments, the processor is configured to determine, from a live ultrasound image of the MR jet, whether the live ultrasound image shows a desired target cardiac view, the desired target cardiac view depending on the selected measurement, and wherein the processor is further optionally configured to provide guidance to the user for positioning the probe with respect to the subject to acquire the desired target cardiac view. For example, responsive to a user selection of the RVol or RV measurement (via the MR exam GUI), the processor is configured to determine whether the live ultrasound image shows an apical 4-chamber (A4C) view and, upon a determination to the contrary, the processor provides guidance for acquiring an A4C view. Each of the different selected measurements may be associated with a different target view. In some embodiments, predictive models (e.g., trained deep learning algorithms) may be used to determine whether the target view is visualized in the image, thus in some instances, the system may include or communicate with memory storing, a plurality of differently trained predictive models, each trained to recognize whether an image represents the desired target view (e.g., an A4C, a parasternal long-axis (PLAX) view, etc.).

In some embodiments of the system, the processor automatically adjusts the acquisition settings to processor-estimated MR-specific TSP settings depending on the automation selection received via the MR exam GUI. For example, if the automated settings tuning mode (e.g., auto-TSP mode) is selected, the system automatically estimates and applies predicted optimal imaging settings to the imaging device. If the automated settings mode is not selected or activated, the system instead provides guidance on the display for manually adjusting one or more of the imaging settings. In some embodiments, the system uses one or more predicative models (e.g., one or more trained convolutional neural networks (CNNs)) to estimate the optimal values for the plurality of imaging settings (e.g., color gain, Nyquist shift, effective frame rate, and excessive image gain) that can affect the quality of the cardiac color Doppler image.

When suitable imaging settings have been applied to the imaging device, the system proceeds to acquire a sequence of ultrasound images of the target view upon which the selected measurement is to be based. In some embodiments, the system instructs the user how to acquire a sufficient sequence of ultrasound images for the selected measurement. For example, in the case of VCW, the system may instruct the user to acquire, or may automatically capture, a sequence of images for at least one full phase (e.g., the systolic phase) of the cardiac cycle. The processor is configured to select one or more frames from the sequence of images for obtaining the selected measurement, and depending upon automation settings selected via an interface screen of the MR exam GUI, the processor may automatically obtain the measurement, in some instances, from the selected one or more frames. The imaging system may then repeat steps of the system-guided process for obtaining remaining ones of the plurality of measurements.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 3 is a process diagram of an MR exam workflow in accordance with the principles of the present disclosure.

FIG. 9 is a block diagram of another configuration of a predictive model comprising a multi-tasking neural network in accordance with the principles of the present disclosure.

DETAILED DESCRIPTION OF EMBODIMENTS

Figure 1:
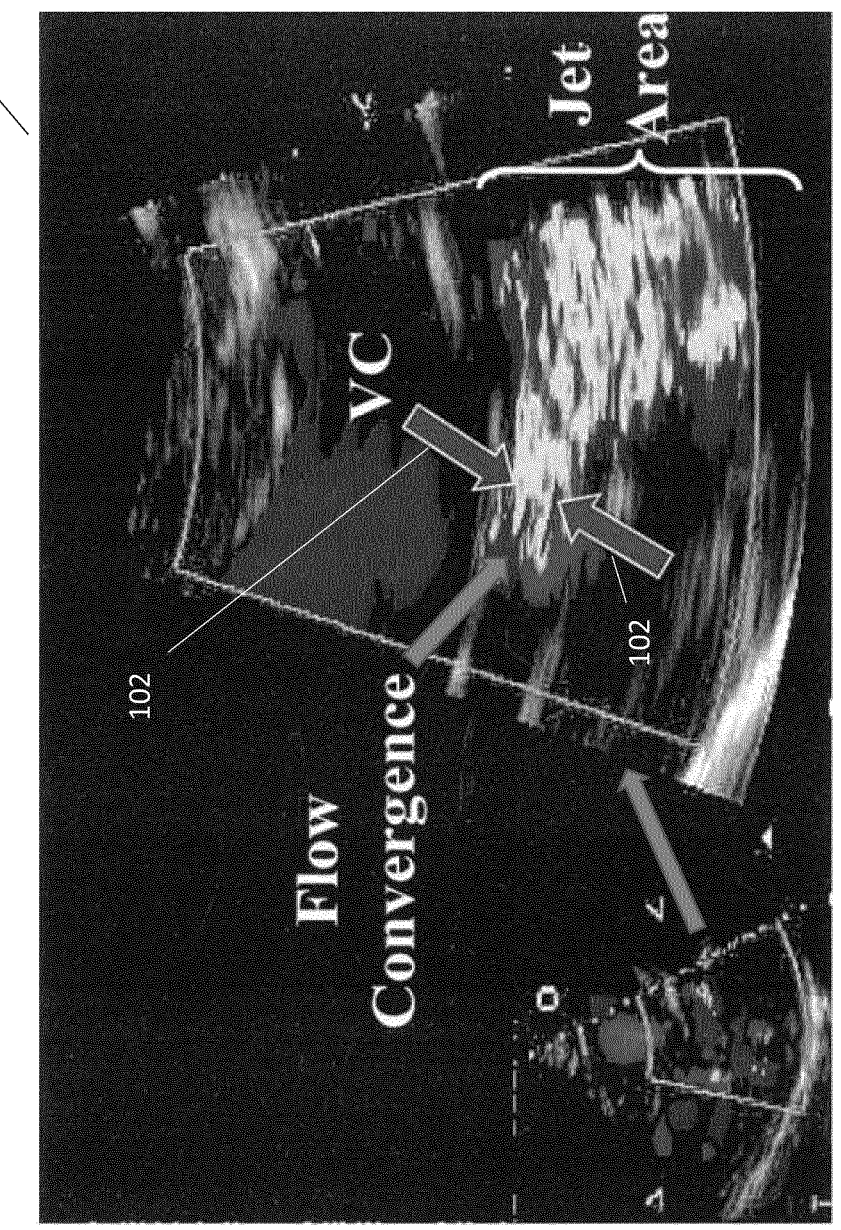
FIG. 1 shows a color Doppler image of an MR jet.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Determining the severity of MR is an important factor in MR management as it carries significant prognostic implications and determines the treatment strategies as well as the timing for surgical intervention if needed. Although clinical guidelines have been published to promote the best practice for MR quantification, accurate quantification of MR severity level remains challenging. Currently, there is a lack of assistance for MR quantification during ultrasound acquisitions and providing such assistance is in critical need.

FIG. 1 shows a color flow image 100 (i.e. a Doppler echocardiogram) of a mitral regurgitation jet obtained from a zoomed view of a parasternal axis, depicting the three components of the regurgitant jet (i.e. the flow convergence, the vena contracta (VC), and the jet are) in a left atrium. As previously described. MR quantification involves imaging the following cardiac features: vena contracta width (VCW) (which is the distance between the two arrows 102 in FIG. 1), regurgitant volume (RVol) and fraction (RF), and effective regurgitant orifice area (EROA). The VCW is typically best imaged in a modified parasternal long-axis view with the transducer laterally translated or angulated, if necessary, to allow complete visualization of the MR jet. A 2-chamber view should not be used because this view is oriented parallel to the line of leaflet coaptation and may exaggerate the MR severity when the MR jet is asymmetrical, with the longer axis occurring through the coaptation line. Once the transducer is positioned in relation to the subject to acquire the appropriate view, the transducer should be adjusted as necessary to obtain the largest MR jet size.

In addition to acquiring the appropriate view, image acquisition settings may need to be adjusted to an optimal setting. For example, the imaging focus should be moved to the valve, and the color sector height and sector width should be minimized to focus on the valve and increase the imaging frame rate. The color sector should be as narrow as possible to maximize lateral and temporal resolution. An aliasing velocity of 50 to 70 cm/s may be used with the color gain set just below the threshold for noise. After image quality is determined to be adequate, each systolic frame should be examined to identify the frame with the largest and best visualized VC. The largest VC can occur at different points in the cardiac cycle depending on the underlying etiology of MR.

The image acquisitions for the additional cardiac parameters (i.e. RVol, RF and EROA) needed to quantify MR, have different criteria for the best view and/or frame as compared to those used to measure the VCW. Imaging guidelines for these additional measurements may similarly be provided but may similarly be challenging to follow, particularly by a novice operator. For example, the best view for measuring RVol and RF is an apical 4-chamber view, where the best cycle for obtaining a measurement is when the image is centered on the mitral annuals. For most accurate measurement, the 4 chamber view should not include any part of the left ventricle outflow tract (LVOT) and atrium and ventricle should not be foreshortened. As previously introduced, following best practices for accurate MR quantification is quite challenging. MR by nature is not always holosystolic—the coaptation defect takes time to develop and thus the biggest MR could happen at any phase of the systolic cycle—early, mid or late. Ultrasound cardiac imaging is a very dynamic exam and it relies on the motion of the heart. Determining the frame in which largest MR jet size is obtained can be quite challenging and is, thus, operator dependent. These is also a lot of subjectivity (e.g., operator's judgement) as to when the MR size is maximized in an image and thus the measurements are further prone to error. Furthermore, the imaging settings affect accuracy of MR quantification, which may profoundly impact the evaluation of MR severity. Non-optimal color gain, Nyquist shift and effective frame rate result in MR overestimation. When the overall color gain is set too high, the MR jet size would be deceivably increased beyond its true size, leading to wrong quantification. Excessive color gain is characterized by the sparkling effects of scattered pixels, which might appear as color noise. Too much of a widening of the color-flow sector is used causes the frame rate to decrease, and low frame rate may increase the MR jet size. True depiction of jet size would be achieved when the maximum temporal sampling is applied. Another factor affecting the jet size is persistence control. With increased persistence parameter, the combination of multiple frames in a moving images could remarkably increase the jet size. Excess B-mode image gain could lead to underestimation of true jet size. By increasing the image gain, low amplitude noise pixels enter the picture. This causes a haze in the image display at the region where color flow pixel representing MR jet should be displayed. Similar problems are encountered for 3D TTE. The transthoracic transducer position or the TEE plane that provides the best 2-dimensional (2D) view of the mitral valve and the MR jet should also be the starting point for the 3-dimensional (3D) acquisition. The methods and system described herein aim to eliminate, from the MR evaluation process, the operator-dependence and thus operator-introduced errors into the MR evaluation process. Thus, the methods and system not only aid in producing more accurate results but also improve reproducibility of the results, since typically multiple MR exams are often needed during MR management and treatment of a patient.

In accordance with the present disclosure, an ultrasound imaging system and method designed to remove operator dependence, and thus reduce or eliminate operator-introduced error from the MR quantification process, is described. The system described herein provides, on an ultrasound imaging device, user-guidance and/or system automation that eliminates a number of operator-subjective decision points in the workflow of an MR exam. According to some embodiments, the ultrasound imaging system for MR quantification includes an ultrasound imaging device, which includes a probe configured to transmit ultrasound into a subject (e.g., a patient) in accordance with the selected acquisition setting and to receive ultrasound echoes for generating ultrasound images of the heart of the subject. The system may further include a display for displaying one or more of the ultrasound images, and a processor in communication with the display and the ultrasound imaging device. The processor is configured to receive one or more live ultrasound images of the heart that show a mitral regurgitation (MR) jet, provide a graphical user interface (GUI) for an MR exam workflow, wherein the GUI is configured to enable a user to selectively activate an auto-TSP mode and to select from a plurality of measurements consisting of vena contracta width (VCW), regurgitant volume and fraction (RVol/RF) and effective regurgitant orifice area (EROA). Furthermore, for each selected measurement of the plurality of measurements, the processor provides measurement-specific user guidance on the display for at least one of positioning the probe, adjusting acquisition settings, and determining a target frame from a sequence of ultrasound images for obtaining the selected measurement.

Figure 2:
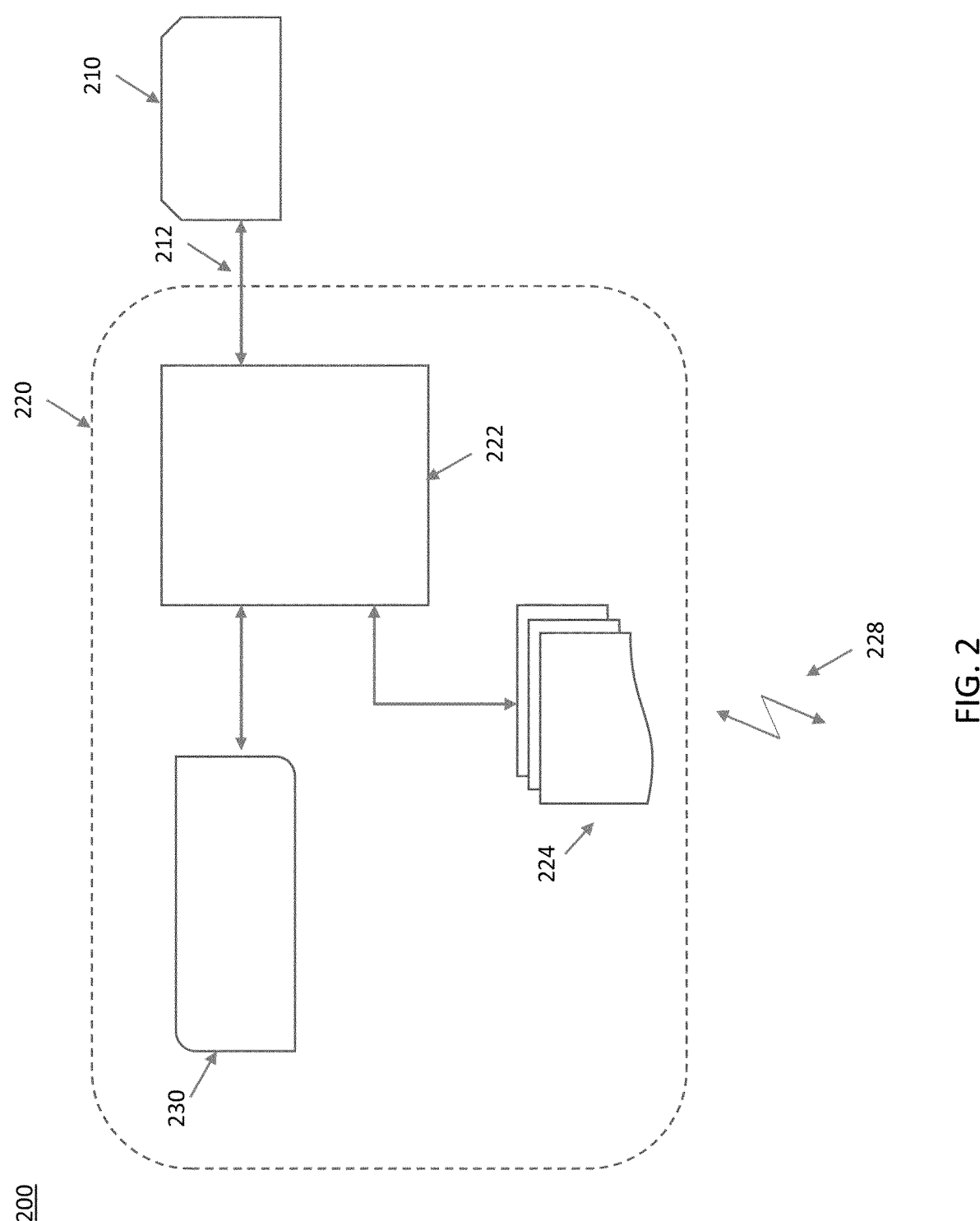
FIG. 2 is a simplified block diagram of a system for ultrasonic MR evaluation according to embodiments of the present disclosure.

A system 200, arranged to perform ultrasound imaging according to aspects of the present disclosure, is shown in FIG. 2. The system 200 is configured for ultrasonically scanning an area or volume of a patient's body, and may thus be referred to as an ultrasound scanner. The system 200 includes a probe 210 which transmits ultrasound into a subject (e.g., a patient's anatomy) and receives ultrasound echoes from which signals are generated and provided to the main processing portion (also referred to as scanner base or host) 220 for generating ultrasound images. The system 200 also includes a user interface 230, which includes one or more displays for displaying the ultrasound images and/or one or more user controls and/or instructions (e.g., GUI elements) associated with performing an MR exam. In some embodiments the user interface 230 includes a primary display which may be used to display images and/or user guidance. The user interface 230 may include a secondary touch-sensitive display, which may display one or more GUI elements, such as GUI controls for initiating the MR exam, for selecting one or more modes associated with the MR exam (e.g., an auto-TSP mode), and for selecting, in sequence, the different MR-specific measurements to be obtain, responsive to which the system-guided sub-work-flows of the MR exam are initiated and performed by the host 220. The secondary display may, in some embodiments, also display ultrasound images generated during the MR exam.

The probe 210 communicates with the host 220 via a communication link 212, such as a serial cable, a USB cable, or other suitable wired or wireless electronic communication link. The probe 210 includes an ultrasound transducer, a beamformer, one or more analog and digital components, and a communication interface, for recording and communicating, via the communication link, the signals detected by the transducer to the base 220. The probe 210 may be in any suitable form for imaging various body parts of a patient, e.g., the heart, while positioned inside or outside of the patient's body. In an embodiment, the probe 210 is an external ultrasound imaging device including a housing arranged to be handheld operation by a user, and thus also referred to as a handheld probe. The probe's transducer may be arranged to obtain ultrasound signals while the user grasps the housing of the probe 210 such that the transducer is positioned adjacent to and/or in contact with a patient's skin. In other embodiments, the probe 210 includes one or more bendable portions allowing it to be positioned and held conformally against the patient's body, and may thus be referred to as a patch-based ultrasound probe. In such embodiments, the probe 210 is arranged to detect and record ultrasound echo signals reflected from the patients's anatomy within the patient's body while the probe 210 remains positioned outside of the patient's body. In some other embodiments, the probe 210 may be in the form of a catheter, an intravascular ultrasound (IVUS) catheter, an intracardiac echocardiography (ICE) catheter, a transesophageal echocardiography (TEE) probe, a transtho-racic echocardiography (TTE) probe, an endo-cavity probe. The probe's transducer may include any suitable array of transducer elements which can be selectively activated to transmit and receive the ultrasound signals for generating images of the anatomy.

The host 220 includes one or more processors, illustra-tively shown as processor 222, which execute, or commu-nicate with one or more external processors that execute, one or more predictive models 224 during the MR exam. The one or more predictive models 224 may be located on the host 220 or remotely, e.g., on a server or other networked computing device with which the host 220 is arranged to communicate (e.g., via a wireless communication link 228). The user interface 230 may present, for example on the touch screen display of the host 220 and responsive to commands from the processor 222, a graphical user interface (GUI) for performing an MR exam as described herein. The processor 222 may receive user inputs via the user interface 230, such as the selection(s) of buttons for initiating the MR workflow, for selecting automation mode(s) and/or selecting the MR measurements, in sequence, to be collected as part of the MR exam. Responsively, the processor 222 may couple ultrasound images to the one or more predicative models 224 for generating user guidance or effecting certain automation during the MR exam, thereby removing user-dependence from the measurements obtained during the exam.

Figure 4A:
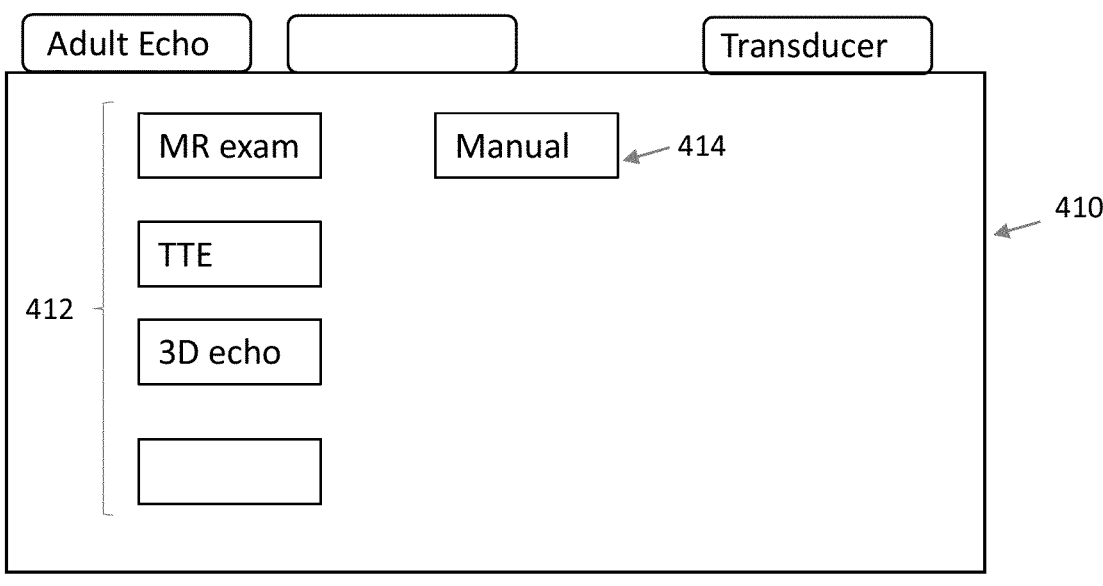
FIGS. 4A and 4B show simplified illustrations of user interface screens associated with an MR exam implemented by an ultrasound scanner of the present disclosure.

FIG. 3 shows an exemplary MR quantification workflow or process 300 for improving the repeatability and reducing user-error during ultrasonic MR evaluation, and which may be implemented by system 200 in accordance with embodi-ments of the present disclosure. Process 300 is described with reference also to FIGS. 4A and 4B that show examples of user interface screens associated with an ultrasonic MR exam according to the present disclosure. At the start of process 300, an MR Exam GUI is displayed. In some embodiments, to initiate the MR workflow or process 300, the scanner 200 may allow the user to select among available exam options when a given transducer type (e.g., an S4-2 or X7-2t transducer on an exemplary PHILIPS imaging sys-tem) has been selected and/or detected by the host 220. For example, as shown in FIG. 4A, when a transducer suitable for cardiac imaging has been connected to the host 220 and/or selected by the user (e.g., via the user interface 230), the user interface 230 may display an interface screen 410 providing one or more exam type options 412 and/or a manual scan option 414 available for the selected/connected transducer type. Different exam options may be presented when a transducer type suitable for a different imaging application (e.g., abdominal, spine, superficial, lung, pelvic, OB/GYN, etc.) is connected and/or selected for use. At some point, before or after selecting the transducer type and/or the exam type, the scanner 200 may provide the user with one or more interface screens for inputting and/or editing the patient information. Upon selection of a cardiac exam and/or the scanner detecting that a probe suitable for cardiac imaging, such as the PHILIPS X7-2t transducer for TTE adult echo or the PHILIPS S4-2 sector array transducer, has been connected to the base, a GUI such as the interface screen 410 shown in FIG. 4A may be provided to enable the user to initiate the MR workflow and associated system-provided automation and guidance.

Figure 4B:
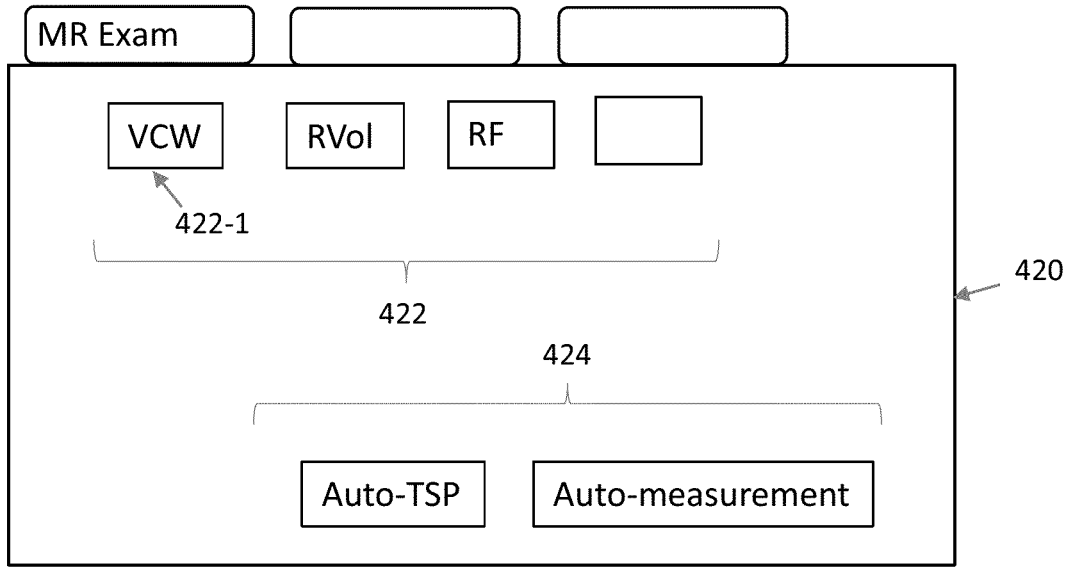

As the workflow 300 progresses, the graphical user inter-face may update to display a sequence of different interface screens for example to display images together with system-provided guidance and/or enable processor-assisted tuning of the acquisition settings. For example, once the MR exam starts, the process continues to a measurement selection step, at which the user may select from one of a plurality of pre-determined measurements (e.g., VCW, RVOL/RF, etc.) associated with the MR exam. For example, and referring to FIG. 4B, once the MR exam has been initiated, the user interface 430 may refresh to display the main MR exam GUI or screen 420, which may include a plurality of GUI elements, such as automation control button 424 and mea-surement selection buttons 422, for setting one or more MR exam options. The selection of any of the measurement selection buttons 422 may each activate a sub-workflow for guiding and/or automating the collection of the selected measurement. The automation control buttons 424 may enable the user to selectively activate and de-activate certain automation functions provided by the processor-assisted MR workflow, as described further below. The GUI ele-ments on the main MR exam interface screen 420 in FIG. 4B are exemplary and shown only for illustration and it will be understood that in some embodiments, the interface screen 420 may include additional GUI elements, fewer GUI ele-ments and/or the elements may be differently arranged on the screen. In some embodiments, the workflow 300 may progress through the collection of each measurement, e.g., in a sequence selected by the user, and may return to the main screen (e.g., the main MR Exam GUI 420) to enable the user to select the next measurement and/or set automation options. In other embodiments, in which the sequence of measurement collection is automated, the main MR Exam GUI may not include measurement selection buttons 422. In some embodiments, the automation functionality may additionally or alternatively be selectable or controllable in the interface screens associated with a specific sub-workflow.

Referring back to FIG. 3, and as shown in block 312, the system receives a selection of a measurement, namely a selection of one of a plurality of predetermined MR measurements (e.g., VCW, RVol or RF, etc.) to be obtained during the MR exam to enable MR quantification. The system may enable the user to select and obtain each of the plurality of measurements in any order desired by the user, and upon a selection of a measurements, the system may launch a sub-workflow associated with the selected measurement. In other embodiments, the order in which the measurements are obtained may be preset in the MR workflow and thus the system may automatically proceed to the next measurement in the sequence once a preceding measurement has been obtained. In such embodiments, the main MR exam GUI may provide only options associated with the level of automation desired by the user. Proceeding to block 314, the system (e.g., scanner 200) acquires and displays live cardiac images. The term live when describing ultrasound images implies that the images are generated and displayed in near real-time as the ultrasound signals are being acquired by the probe, as compared to images that are previously recorded, such as during a prior exam. As the system (e.g., scanner 200) acquires and displays the images of the heart, the system determined whether the images displayed show a desired target view. The target view to which the system matches the displayed images depends upon the selected/active measurement workflow that is being executed. For example, if the selected measurement is VCW, the target view is parasternal long-axis (PLAX) view. Thus, when the system is progressing through the sub-workflow for obtaining the VCW measurement, the system is processing the live images to determine if they represent a PLAX view. If the selected measurement is RVol or RF, the target view is apical 4-chamber (A4C) view, and thus if the system is executing the sub-workflow for obtaining the RVol or RF measurements, the system is processing the live images to determine if they represent a A4C view. In some embodiments, the system optionally provides guidance to the user for positioning the probe on the subject's body for acquiring the target view. For example, the system may display a body marker or other suitable graphic showing simplified illustration of the body and showing the placement of the probe in relation to the human body. In some embodiments, the processor may use image segmentation, image classification, or various other techniques to determine whether the anatomy in the first image corresponds to the target view. In some embodiment, the system may additionally or alternatively process the live images to determine navigation instructions for guiding the user's placement of the probe. Any suitable technique for optionally providing guidance to a user to properly position the probe on the subject's body to acquiring the target view may be used without departing from the scope of the present disclosure.

In some scenarios, such as in some of the sub-workflows associated with the different measurements, the system (e.g., scanner 200) may additionally provide user guidance for probe adjustments in the target view to ensure the relevant feature(s) of mitral valve regurgitation is properly visualized. For example, when the selected measurement is VCW, the system may process the live images that capture a PLAX view to determine whether the MR jet is fully visualized in the images. If the MR jet is not fully visualized, the system may provide guidance, such as on the display, for fine-tuning positional adjustments (e.g., translation and/or angulation of the probe) while maintaining the probe in the acoustic window for capturing a PLAX view. This guidance may be provided in accordance with any of the examples herein, as will be described further below. Once the probe is in the acoustic window for the target view (e.g., a PLAX view) and optionally adjusted to a position within that window to fully visualize the relevant anatomical feature(s), the workflow proceed to an acquisition setting optimization step, as shown in block 318. In this step, and based on the selected level of automation (at block 312), the system (e.g., scanner 200) may either provide guidance to the user for manually tuning the acquisition settings to settings estimated by the processor as suitable or optimal for the selected measurement, or the system may automatically apply the processor-estimated optimal settings. The processor-estimated optimal settings may be different for each MR quantification measurement, and they may be also referred to, for simplicity, as MR-specific settings. Next, with the scanner set to the MR-specific settings, a sequence of ultrasound images are acquired of the target view and for a predetermined minimum duration (e.g., at least a full cardiac cycle, or at least one full phase, such as a full systolic phase, of the cardiac cycle). Again, the predetermined minimum duration for the sequence of images may differ and/or depend upon the selected measurement and thus, the sub-workflow being executed by the system. The system may guide the user in this regards, such as by instructing the user to hold the probe in position for a certain period of time and/or sound a beep or display a completion indicator when a sufficiently long cineloop for the selected measurement has been recorded.

The workflow then proceeds to block 322 at which the system (e.g., processor 222) determines, from the sequence of images recorded in block 320, one or more target frames based on which the selected measurement is to be made, as further described below. Next the selected measurement is obtained from the one or more processor-selected frames, as shown in block 324. The measurement may be made manually by the user, or it may be automatically obtained by the system, depending on the level of automation selected, e.g., at block 312. It will be understood that while automation selections are shown in this example, for simplicity, as occurring prior to the start of the exam, in some embodiments, the sequence of interface screens of the GUI may be configured to enable the user to activate and deactivate certain automation features throughout the exam. For example, the workflow may present one or more GUI elements at block 324 that allow the user to activate the automated measurement feature, or to deactivate it if it was previously selected. After the selected measurement is obtained, the process 300 proceeds to block 326, at which the GUI updates to return to the main MR Exam GUI and enable selection of another one of the plurality of predetermined measurements associated with the MR workflow, following which the process 300 may repeat for the newly selected measurement. In some embodiments in which the sequence automatically progresses through the different measurements, this step may be omitted. If the system determines that all measurements associated with the MR workflow have been recorded, the system exits the MR workflow and process 300 terminates.

Figure 5:
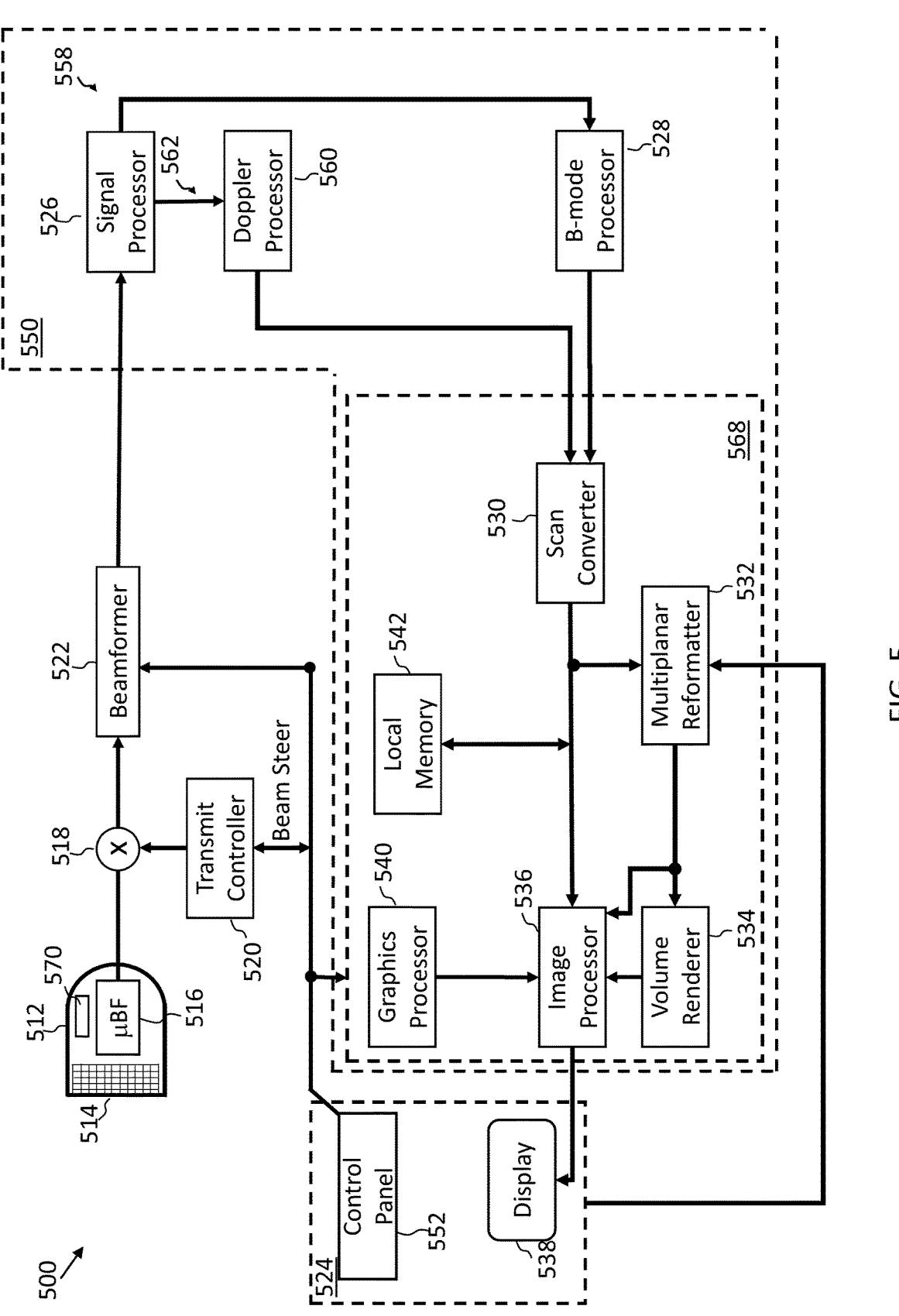
FIG. 5 is a block diagram of an ultrasound imaging system in accordance with the principles of the present disclosure.

System 200 and process 300 may be implemented by an ultrasound imaging system having components as shown and further described with reference to FIG. 5. The ultrasound imaging system 500 includes a transducer array 514, which may be included in an ultrasound probe 512, for example an external probe such as one suitable for transthoracic echocardiography (TTE) or an internal probe such as one suitable for transesophageal echocardiography (TEE). The transducer array 514 is configured to transmit ultrasound signals (e.g., beams, waves) and receive echoes responsive to the ultrasound signals. A variety of transducer arrays may be used, e.g., linear arrays, curved arrays, or phased arrays. The transducer array 514, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction. In some embodiments, the probe 512 may include one or more sensors 570 associated with a position or motion tracking system. In some examples, the sensor 570 is provided by an IMU which may include an accelerometer, a gyroscope, a magnetometer, and/or a combination thereof. The IMU may provide data relating to the velocity, acceleration, rotation, angular rate, and/or orientation of the probe 512. In some embodiments the sensor 570 includes an EM sensor which is associated with an EM tracking system that tracks the position of the sensor 570 on the probe. In some embodiments the one or more sensors 570 may be a combination of motion and position tracking sensor(s). Any data provided by or responsive to sensor 570 may be referred to collectively as probe position or motion data depending on the type of sensor used.

In some embodiments, the transducer array 514 may be coupled to a microbeamformer 516, which may be located in the ultrasound probe 512, and which may control the transmission and reception of signals by the transducer elements in the array 514. In some embodiments, the microbeamformer 516 may control the transmission and reception of signals by active elements in the array 514 (e.g., an active subset of elements of the array that define the active aperture at any given time). In some embodiments, the microbeamformer 516 may be coupled, e.g., by a probe cable or wirelessly, to a transmit/receive (T/R) switch 518, which switches between transmission and reception and protects the main beamformer 522 from high energy transmit signals. In some embodiments, for example in portable ultrasound systems, the T/R switch 518 and other elements in the system can be included in the ultrasound probe 512 rather than in the ultrasound system base, which may house the image processing electronics. An ultrasound system base typically includes software and hardware components including circuitry for signal processing and image data generation as well as executable instructions for providing a user interface (e.g., processing circuitry 550 and user interface 524). The transmission of ultrasonic signals from the transducer array 514 under control of the microbeamformer 516 is directed by the transmit controller 520, which may be coupled to the T/R switch 518 and a main beamformer 522. The transmit controller 520 may control the direction in which beams are steered. Beams may be steered straight ahead from (orthogonal to) the transducer array 514, or at different angles for a wider field of view. The transmit controller 520 may also be coupled to a user interface 524 and receive input from the user's operation of a user control. The user interface 524 may include one or more input devices such as a control panel 552, which may include one or more mechanical controls (e.g., buttons, encoders, etc.), touch sensitive controls (e.g., a trackpad, a touchscreen, or the like), and/or other known input devices. The transmission of signals (i.e. acoustic energy) from the transducer array 514, under the control of transmit controller 520, occur in accordance with acoustic settings, also referred to as imaging or acquisition settings, and which may be manually set by the user (e.g., via the user interface 524) or at least partially automatically set by a processor of the system 500.

In some embodiments, partially beamformed signals produced by the microbeamformer 516 are coupled to a main beamformer 522 where partially beamformed signals from individual patches of transducer elements may be combined into a fully beamformed signal. In some embodiments, microbeamformer 516 is omitted, and the transducer array 514 is under the control of the main beamformer 522 which performs all beamforming of signals. In embodiments with and without the microbeamformer 516, the beamformed signals of the main beamformer 522 are coupled to processing circuitry 550, which may include one or more processors (e.g., a signal processor 526, a B-mode processor 528, a Doppler processor 560, and one or more image generation and processing components 568) configured to produce an ultrasound image from the beamformed signals (e.g., beamformed RF data).

The signal processor 526 may be configured to process the received beamformed RF data in various ways, such as bandpass filtering, decimation, I and Q component separation, and harmonic signal separation. The signal processor 526 may also perform additional signal enhancement such as speckle reduction, signal compounding, and noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 558 which couples the signals from the signal processor 526 to a B-mode processor 528 for producing B-mode image data. The B-mode processor can employ amplitude detection for the imaging of structures in the body. The signals produced by the B-mode processor 528 may be coupled to a scan converter 530 and/or a multiplanar reformatter 532. The scan converter 530 may be configured to arrange the echo signals from the spatial relationship in which they were received to a desired image format. For instance, the scan converter 530 may arrange the echo signal into a two dimensional (2D) sector-shaped format, or a pyramidal or otherwise shaped three dimensional (3D) format. The multiplanar reformatter 532 can convert echoes which are received from points in a common plane in a volumetric region of the body into an ultrasonic image (e.g., a B-mode image) of that plane, for example as described in U.S. Pat. No. 6,443,896 (Detmer). The scan converter 530 and multiplanar reformatter 532 may be implemented as one or more processors in some embodiments.

A volume renderer 534 may generate an image (also referred to as a projection, render, or rendering) of the 3D dataset as viewed from a given reference point, e.g., as described in U.S. Pat. No. 6,530,885 (Entrekin et al.). The volume renderer 534 may be implemented as one or more processors in some embodiments. The volume renderer 534 may generate a render, such as a positive render or a negative render, by any known or future known technique such as surface rendering and maximum intensity rendering.

In some embodiments, the system may include a Doppler signal path 562 which couples the output from the signal processor 526 to a Doppler processor 560. The Doppler processor 560 may be configured to estimate the Doppler shift and generate Doppler image data. The Doppler image data may include color data which is then overlaid with B-mode (i.e. grayscale) image data for display. The Doppler processor 560 may be configured to filter out unwanted signals (i.e., noise or clutter associated with non-moving tissue), for example using a wall filter. The Doppler processor 560 may be further configured to estimate velocity and power in accordance with known techniques. For example, the Doppler processor may include a Doppler estimator such as an auto-correlator, in which velocity (Doppler frequency, spectral Doppler) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some embodiments, the velocity and/or power estimates may undergo further threshold detection to further reduce noise, as well as segmentation and post-processing such as filling and smoothing. The velocity and/or power estimates may then be mapped to a desired range of display colors in accordance with a color map. The color data, also referred to as Doppler image data, may then be coupled to the scan converter 530, where the Doppler image data may be converted to the desired image format and overlaid on the B-mode image of the tissue structure to form a color Doppler or a power Doppler image. In some examples, the power estimates (e.g., the lag-0 autocorrelation information) may be used to mask or segment flow in the color Doppler (e.g., velocity estimates) before overlaying the color Doppler image onto the B-mode image.

Outputs from the scan converter 530, the multiplanar reformatter 532, and/or the volume renderer 534 may be coupled to an image processor 536 for further enhancement, buffering and temporary storage before being displayed on an image display 538. A graphics processor 540 may generate graphic overlays for display with the images. These graphic overlays can contain, e.g., standard identifying information such as patient name, date and time of the image, imaging parameters, and the like. For these purposes the graphics processor may be configured to receive input from the user interface 524, such as a typed patient name or other annotations. The user interface 524 can also be coupled to the multiplanar reformatter 532 for selection and control of a display of multiple multiplanar reformatted (MPR) images.

The system 500 may include local memory 542. Local memory 542 may be implemented as any suitable non-transitory computer readable medium (e.g., flash drive, disk drive). Local memory 542 may store data generated by the system 500 including ultrasound images, executable instructions, imaging parameters, training data sets, or any other information necessary for the operation of the system 500. In some examples, local memory 542 may include multiple memories, which may be the same or of different type. For example, local memory 542 may include a dynamic random access memory (DRAM) and a flash memory. In some embodiments, the system 500 may use predictive models, such as a convolutional neural network (CNN), a recurrent neural network (RNN), an autoencoder neural network or other machine learning models trained to perform specific functions. In some embodiments, the trained predictive models may be stored locally on the system (e.g., in local memory 544). In other embodiments, the system 500 may communicated with a networked storage device that stores one or more of the predictive models used by the system 500. In some embodiments, the trained predictive models may be further trained for continually improving their performance with data recorded by and/or stored in the local memory 542 of the system 500.

As mentioned previously system 500 includes user interface 524. User interface 524 may include one or more displays 538 and control panel 552. The display(s) 538 may include one or more display devices implemented using a variety of known display technologies, such as LCD, LED, OLED, or plasma display technology. In some embodiments, the system includes multiple displays 538, such as a main display and a touch screen display. The user interface 524 may also be configured to receive user inputs (e.g., exam type, imaging parameters). To that end, the user interface 524 may include one or more hard controls (e.g., buttons, knobs, dials, encoders, mouse, trackball or others) and one or more soft controls (e.g., GUI control elements or simply, GUI controls) provided on a touch screen display. The various controls of the user interface 524 may be collectively referred to as control panel 552. In some embodiments, various components shown in FIG. 5 may be combined. For instance, the multiplanar reformatter 532 and volume renderer 534 may be implemented as a single processor. In some embodiments, various components shown in FIG. 5 may be implemented as separate components. For example, signal processor 526 may be implemented as separate signal processors for each imaging mode (e.g., B-mode, Doppler). In another example, the image processor 536 may be implemented as separate processors for different tasks and/or parallel processing of a same task. In some embodiments, one or more of the various processors shown in FIG. 5 may be implemented by general purpose processors and/or microprocessors configured to perform the specified tasks. In some examples, the processors may be configured by providing instructions for the tasks from a non-transitory computer readable medium (e.g., from local memory 542). The instructions may then be executed by the processors. In some embodiments, one or more of the various processors may be implemented as application specific circuits. In some embodiments, one or more of the various processors (e.g., image processor 536) may be implemented with one or more graphical processing units (GPU).

In accordance with examples of the present disclosure, the system 500 may be configured to implement an MR exam process which includes providing user guidance and/or automation at one or more steps of the MR exam. To that end, processor-executable instructions may be stored in memory (e.g., local memory 542) which when executed by a processors (e.g., processor 536) of imaging system (e.g., system 500) may cause the system to perform the steps of the MR exam process, such as to display interface screens associated with the MR exam, receive selections from the user, invoke sub-workflows associated with each selected measurement, provide user guidance and/or automate the tuning of acoustic settings and/or collection of measurements. Further details of the process are described with reference also to FIG. 6 in the context of one of the measurements obtained during the MR exam process. However it will be understood that processor-executable instructions may be stored and executed similarly for each of the other measurements to aid the user in accurately and repeatably conducting an MR quantification.

Figure 6:
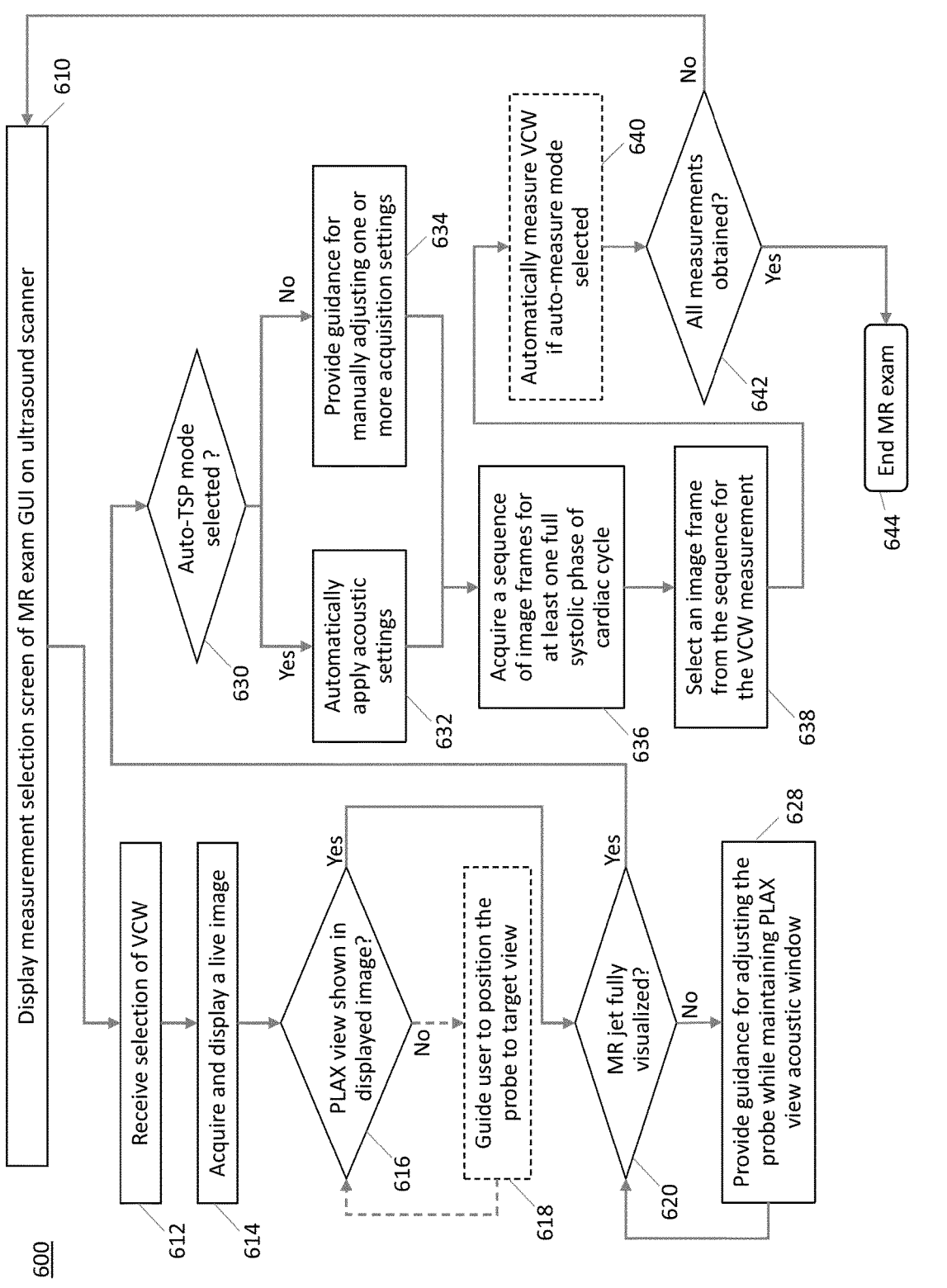
FIG. 6 is a flow diagram of a process for obtaining an MR measurement using an ultrasound scanner according to the present disclosure.

FIG. 6 shows a block diagram of sub-process (or sub-workflow) 600 executed by processor (e.g., processor 222 or 568) upon selection of a particular MR measurement, in this case VCW. As shown at block 610 in FIG. 6, the ultrasound scanner displays the measurement selection screen of the MR exam GUI (e.g., interface screen 420). At block 612, the processor (e.g., processor 222 or 568) receives a selection of VCW responsive to the user pressing the VCW measurement button 422-1 (in FIG. 4B). At block 614, the scanner acquires and displays live ultrasound images. The processor may determine whether a PLAX view is shown in the displayed image (block 616) and may optionally provide guidance (block 618) to the user for positioning the probe relative to the subject's body to acquire a PLAX view. As previously described, this can be by way of a body marker displaying the probe's placement relative to the subject's body. The guidance may alternatively or additionally include image segmentation to determine whether an expected grouping and arrangement of anatomical features appear in the live image(s), which would indicate proper positioning of the probe. In some embodiments, the processor may implement or communicate with a predictive model trained to do image classification and/or segmentation for comparing the live images to the expected view, in this case a PLAX view.

Once the probe is positioned in the appropriate acoustic window to acquire a PLAX view of the heart, the processor determines whether an MR jet if suitably visualized in the view (block 620). The probe may need to be adjusted to a modified PLAX view to fully visualize the MR jet, and the system provides guidance (block 628) for adjusting the probe to the modified PLAX view in which the MR jet is fully visualized. At this stage, the system may instruct the user to turn on the color Doppler feature so that flow can be visualized in the images and thus the MR jet components can be more easily identified by the system. The system may instruct the user to translate and/or angulate the probe while keeping the probe in the PLAX acoustic window and imaging in the color Doppler mode. The system processes the color Doppler image frames to determine the quality of the visualization of the MR jet. As the user adjusts the probe, the system may display a quality indicator that provides visual feedback to the user on whether the probe has achieved the modified PLAX view for suitably visualizing the MR jet. The quality indicator may be a simple visual indicator, such as a green check marker or green light, which is displayed when the system determines that the probe is in an optimal position to fully visualize the MR jet. In some instances, the quality indicator may be a scale (e.g., hot/cold or other scale-based) indicator that dynamically shows whether the probe position is getting closer or farther from the optimal position for a modified PLAX view that fully visualizes the MR jet.

Figure 7A:
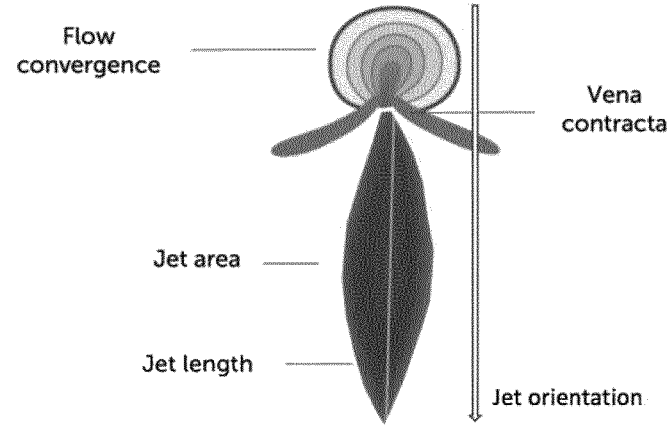
FIGS. 7A and 7B illustrate components of a MR jet and MR jet directions, respectively.
Figure 7B:
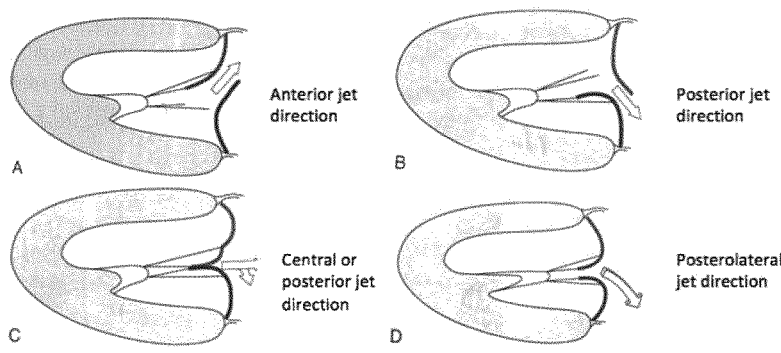

In some embodiments, the system uses a predictive model to determine whether the MR jet is suitably visualized in the image. For a complete MR jet visualization, all the components of the MR jet should be present in the image, which includes the flow convergence region, the vena contracta, and the downstream expansion of the jet (see FIG. 7A) and the probe should be as parallel to the direction of the jet as possible. In other words, the azimuthal direction of the probe should be substantially aligned with the direction of the jet, with all components of the jet visible in the image. The jet direction may generally be classified as anterior, posterior, central or a mix, as shown in FIG. 7B. Thus, a generally parallel placement of the probe would visualize a substantially central jet direction with all components of the MR jet present in the view. A predictive model such as a deep learning, classification model (e.g., a convolutional neural network (CNN) or other suitable neural network) can be trained to determine whether the MR jet represented in each of the color Doppler images is anterior, posterior, central, or a mix, and based on this classification, the system may output the quality metric associated with each dynamically changing position of the probe (as the user adjusts—translate and/or angulates the probe within the PLAX window). Additionally and optionally, the system may guide the user to rotate around the MR jet's direction for a certain range of angles to search (with dynamic visual feedback) for the best angle that visualizes the MR jet, and/or to translate the probe along the MR jet direction (e.g., towards LA) to identify (with visual dynamic visual feedback) the optimal position. Additionally or alternatively, image segmentation may be used to identify, such as by extracting the color pixel areas in the image, the components of the MR jet in the image(s). The width to length ratio and shape of components of the MR jet and/or the color information representing velocity may additionally or alternatively be used to make predictions as to the quality of the visualization of the MR jet. In other words, instead of (or additionally to) labeling training images based on the MR jet direction being classified as either anterior, posterior, central or mix, the images may be labeled based on spatial characteristics of the jet in the image such as width to length ratio, shape, velocity, etc. A classification network may then be trained to output a binary output, such as 0 being insufficient visualization and 1 being sufficient visualization, or decimal values ranging between 0 and 1 in the case of a scale-based feedback.

In other instances, such as when executing a sub-workflow associated with a different MR measurement, the system may apply a different predictive model at this stage to identify the optimal view for the measurement, such as by identifying the presence or absence of a specific anatomical feature in the target view. For example, when the selected measurement is RVol or RF, the predictive model may be trained to detect the presence of the left ventricular outflow tract (LVOT) in the A4C view and the system may reject—i.e. identify as unsuitable—any image which includes any portion of the LVOT in the image.

Returning to FIG. 6, and once the proper modified PLAX view has been acquired, the system proceeds to the acoustic settings tuning portion of the process, starting at block 630. If the user has selected the automated settings mode (e.g., Auto-TSP as shown in block 630), the processor generates estimated optimal settings for the selected measurement (here for the VCW). These processor-generated settings are then automatically applied, without the user manually tuning these acquisition settings, by the processor automatically adjusting the one or more of the acquisition settings of the scanner to the estimated optimal setting (block 632). Alternatively, if the user has not selected the automated settings mode, the system instead provides guidance to the user, such as on the display, for manually adjusting one or more imaging settings to suitable or optimal setting(s) for the selected measurement. The system may use one or more predictive model(s) to estimate the suitable or optimal settings for a given measurement.

For example, and turning now also to FIG. 7, a color Doppler image 802 of the target view is provided as input to each of a plurality of predictive models 804 (e.g., differently trained neural networks), each of which is configured to output an estimation of the suitability of one of a plurality of imaging settings 806. For example a first predictive model 804-1 that receives the input image 802 is configured to predict whether a first imaging setting 806-1 (e.g., the color gain setting) is suitable/optimal—that is, whether it minimizes undesirable artifacts, such as haze effect, and/or otherwise optimizes the visualization of certain anatomical features. The second predictive model 804-2 also receives image 802 as input. The second predictive model 804-2 however is configured to determine if a second imaging setting 806-2 (e.g., Nyquist shift setting) is suitable/optimal. Similarly, a third predicative model 804-3 is configured to determine if a third imaging setting 806-3 (e.g., frame rate setting) is suitable/optimal, and a fourth predictive model 804-4 is configured to determine whether a fourth imaging setting 806-4 (e.g., image gain) is suitable/optimal, based on the same input image 802. Any suitable number n of individually trained models may be used the desired number n of settings for which the system automates and/or guides the tuning of. That is, the system may use fewer or larger number of individually trained models in other embodiments, that the example shown in FIG. 8A. The models 804 may be configured to provide to the processor of the ultrasound scanner a binary output such as a label of 0 or 1 (0 indicating unsuitable or sub-optimal and 1 indicating suitable or optimal) for their respective image setting and the processor may provide visual feedback (e.g., a green check mark or red/green light) to the user on the display for each setting being adjusted. In this example, each of the multiple models evaluates the same image but with respect to the optimal setting for a different imaging parameter and provides its output, which may be collectively displayed to the user, for example in a table listing each of the settings with system-assisted tuning and providing the model's determination for each setting together on the display. The user may continue to manually adjust each of the settings until a positive indicator is displayed for each setting. In this mode, the user may be allowed to proceed to the next step of the workflow without optimizing each setting. In some embodiments, the predictive models may output a confidence score (e.g., a percentage or a non-integer value between 0-1) indicating the likelihood that the setting is suitable/optimal. The processor may convert confidence score(s) of the model (s) to corresponding binary (good/poor) output for generating the user feedback, such as by applying threshold (e.g., all confidence scores below 65% (or 0.65) are deemed poor), or in some cases, the visual feedback to the user may be provided in a form that captures the confidence score, such as by any suitable percentage indicator. The feedback may be provided dynamically, in real time as the user manually tunes each setting. That, when a new setting is applied responsive to the user manually adjusting the setting, a new image is provide to each of the plurality of predictive models and the suitability output (e.g., binary or confidence score) is output by each model for each setting and displayed to the user. In some cases, adjusting one setting may adversely affect another setting and with the dynamic feedback provided by the system, the user is able to visualize these effects. In some embodiments, because of the interplay of the different imaging settings, the system may use a combined, multitasking model that outputs a set of predicted optimal settings, as will be described further below with reference to FIG. 9.

Figure 8A:
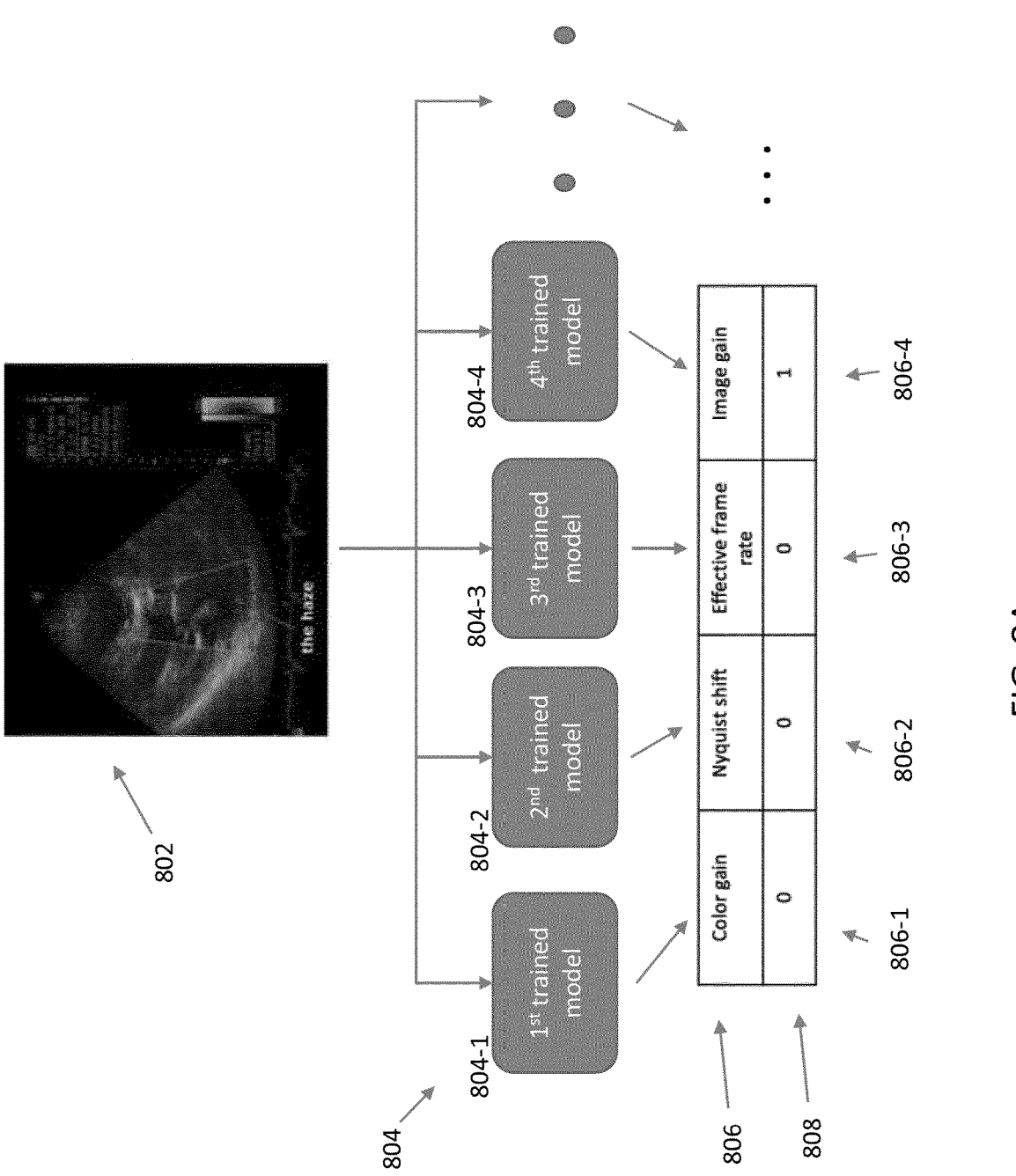
FIG. 8A is a block diagram of an example arrangement of predictive models trained to estimate optimal imaging settings for MR evaluation, and showing inputs and outputs of the models.
Figure 8B:
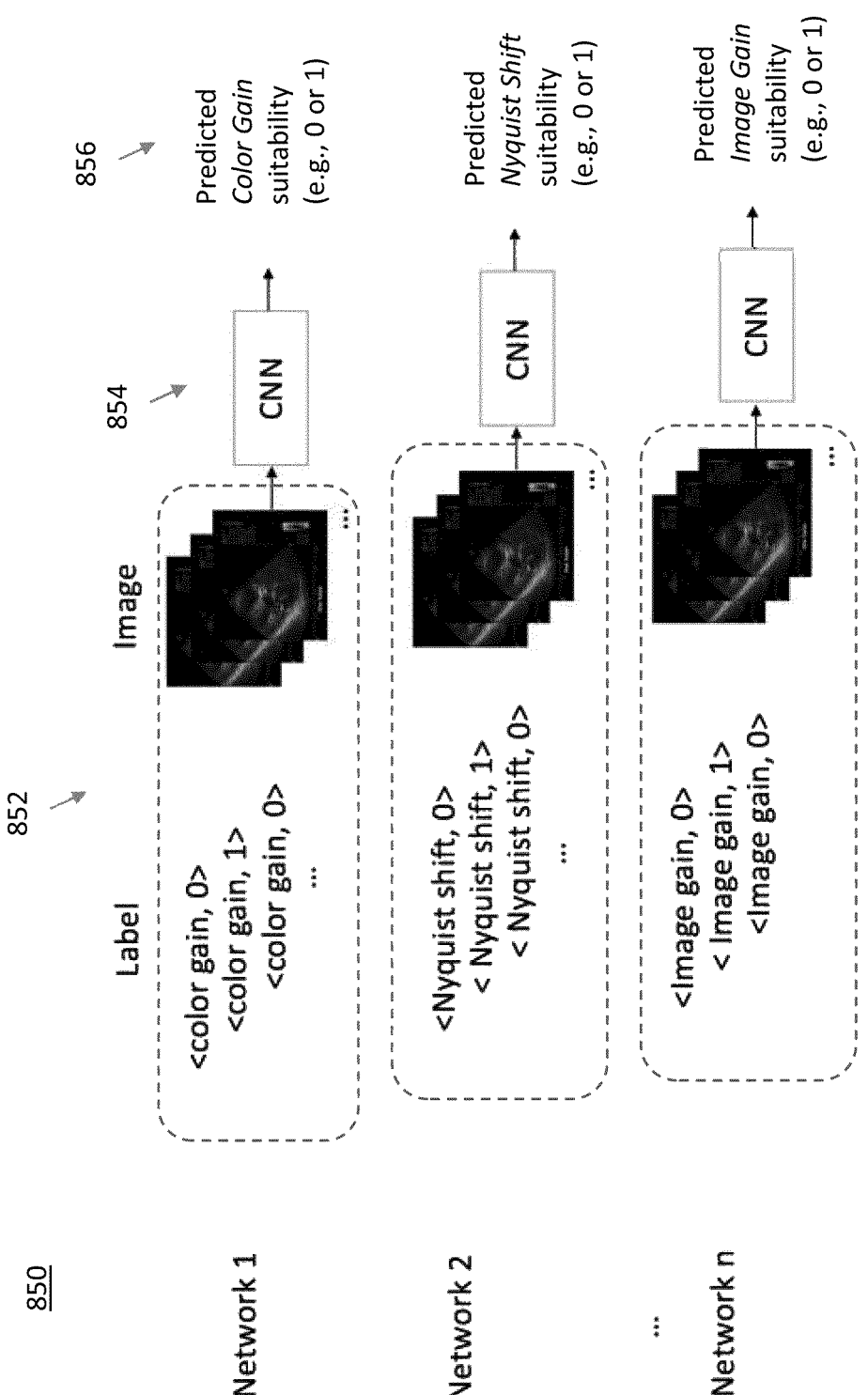
FIG. 8B is a block diagram of a training environment for training the predictive models of FIG. 8A.
Figure 10:
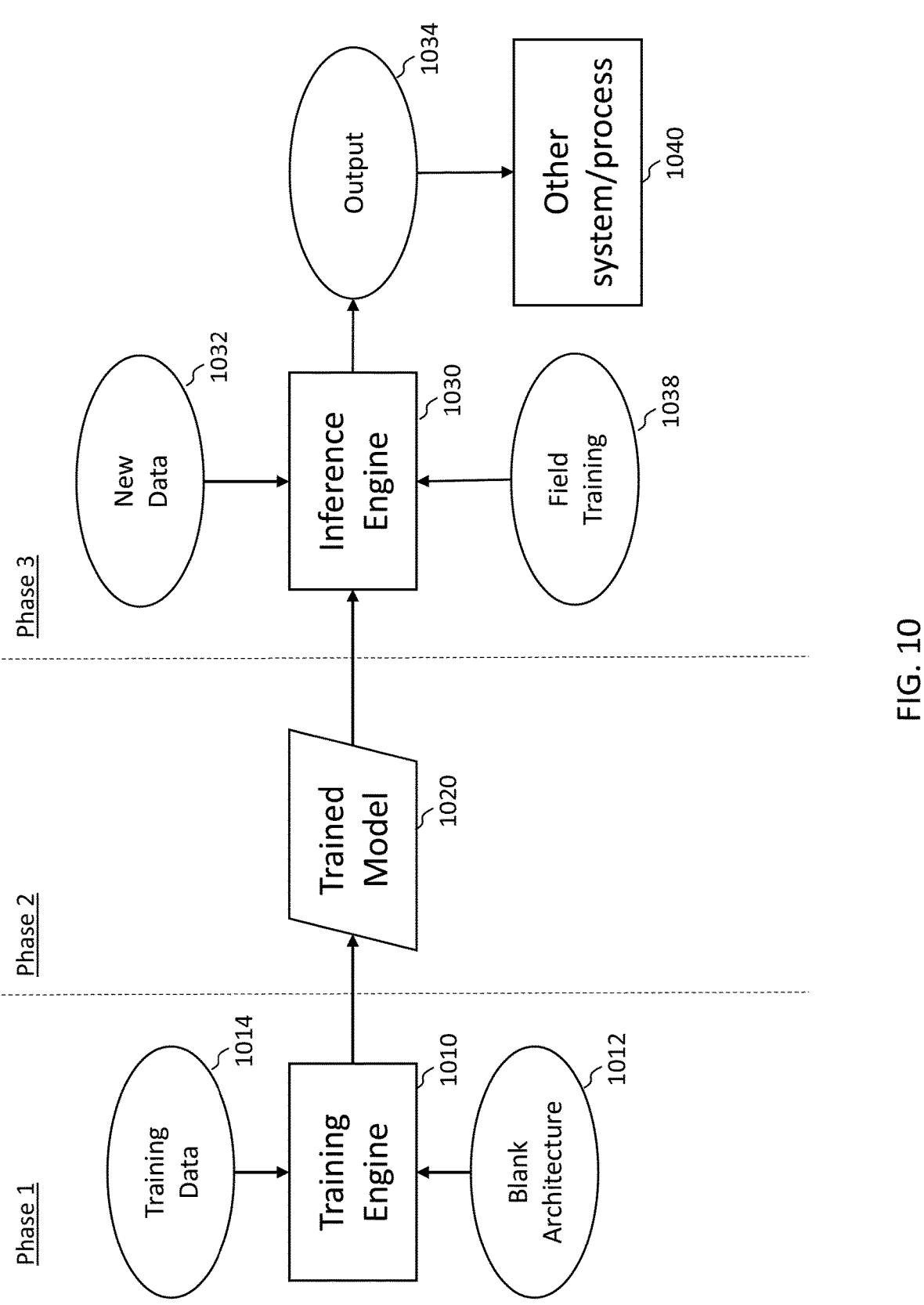
FIG. 10 is a block diagram of a process for training and deployment of a neural network in accordance with the principles of the present disclosure.

FIG. 8B shows an exemplary training scenario 850 for training a plurality of different predictive models, shown here as individual CNNs 854, to train each to classify the suitability of a given imaging setting. During the training phase, each model is trained with sets of training data comprising multiple (hundreds often thousands) of pre-acquired and labeled images. Each image has been labeled with a value (of the desired format to be trained to the network) for the specific imaging setting to be trained to the network. The training data is provided to the individual network 854 and outputs 856 recorded. The parameters of the network (e.g., weights and bias) are tuned iteratively via this process to enhance the performance of the network (e.g., towards a convergence with ground truth). Once sufficiently trained, the networks are ready to be deployed on a point of care system, such as an ultrasound scanner used for MR evaluation of a patient. The training and deployment of exemplary networks is described further below with reference to FIG. 10.

Figure 8C:
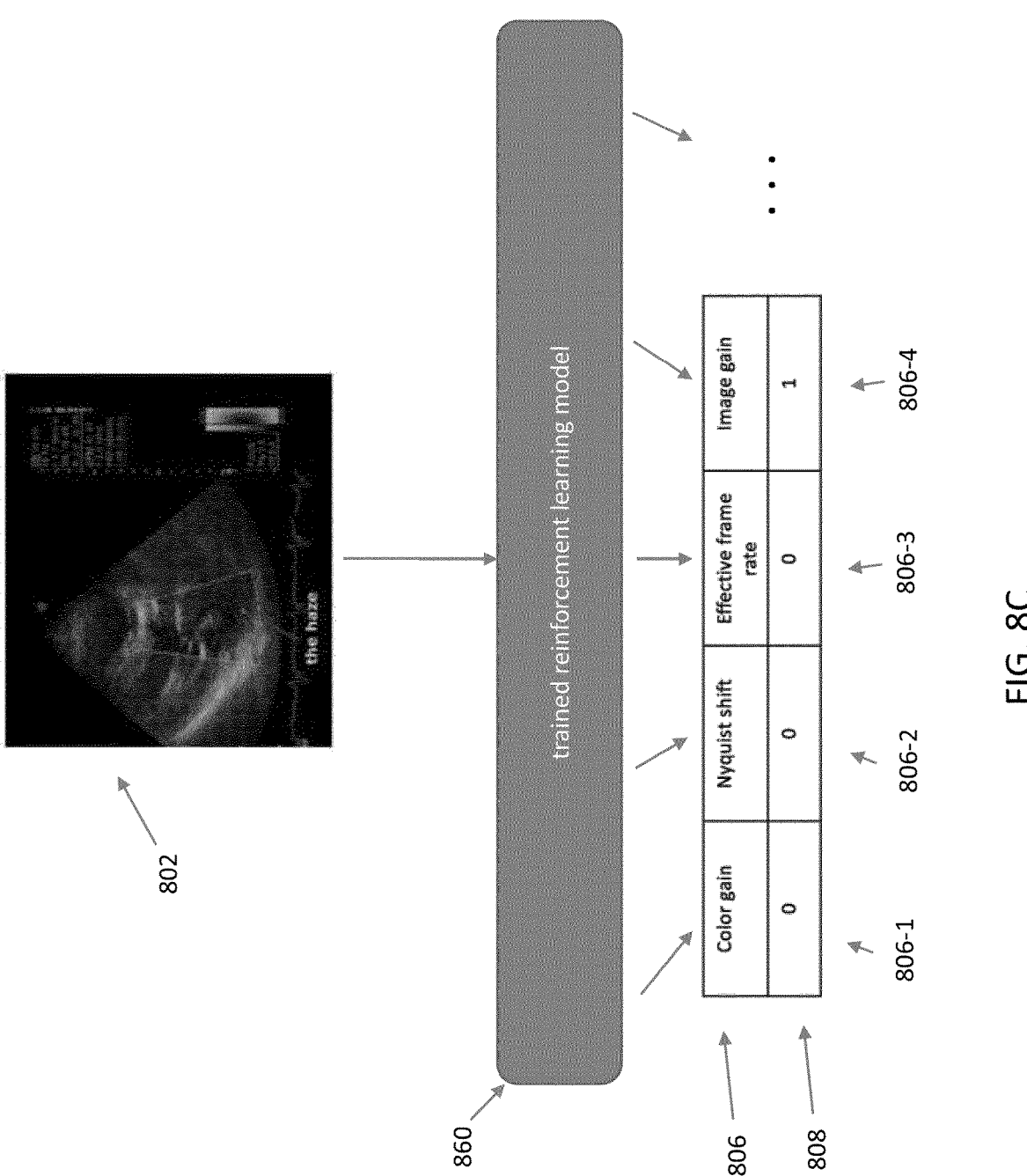
FIG. 8C is a block diagram of another example arrangement of a predictive model trained to estimate a plurality of optimal imaging settings for an MR evaluation.

In yet further examples, a reinforcement learning model as shown in FIG. 8C may be used, where instead of using "labeled" or ground truth images as the training data, the model architecture is configured to maximize a reward function. The reward function may be based, for example, on the image quality and thus a single trained reinforcement-learning model 860 may be used to guide the selection of each of the plurality of settings. The reinforcement-learning model 860 is trained to output a plurality of image settings that maximize the image quality. This plurality of image settings can include any predetermined number of image settings, such as first image setting 806-1 (e.g., color gain setting), second image setting 806-2 (e.g., Nyquist shift setting), third image setting 806-3 (e.g., frame rate setting), fourth image setting 806-4 (e.g., image gain), any/or any other setting(s) which may affect the quality of an acquired image, and which may thus be tuned to maximize the image quality.

Figure 9:
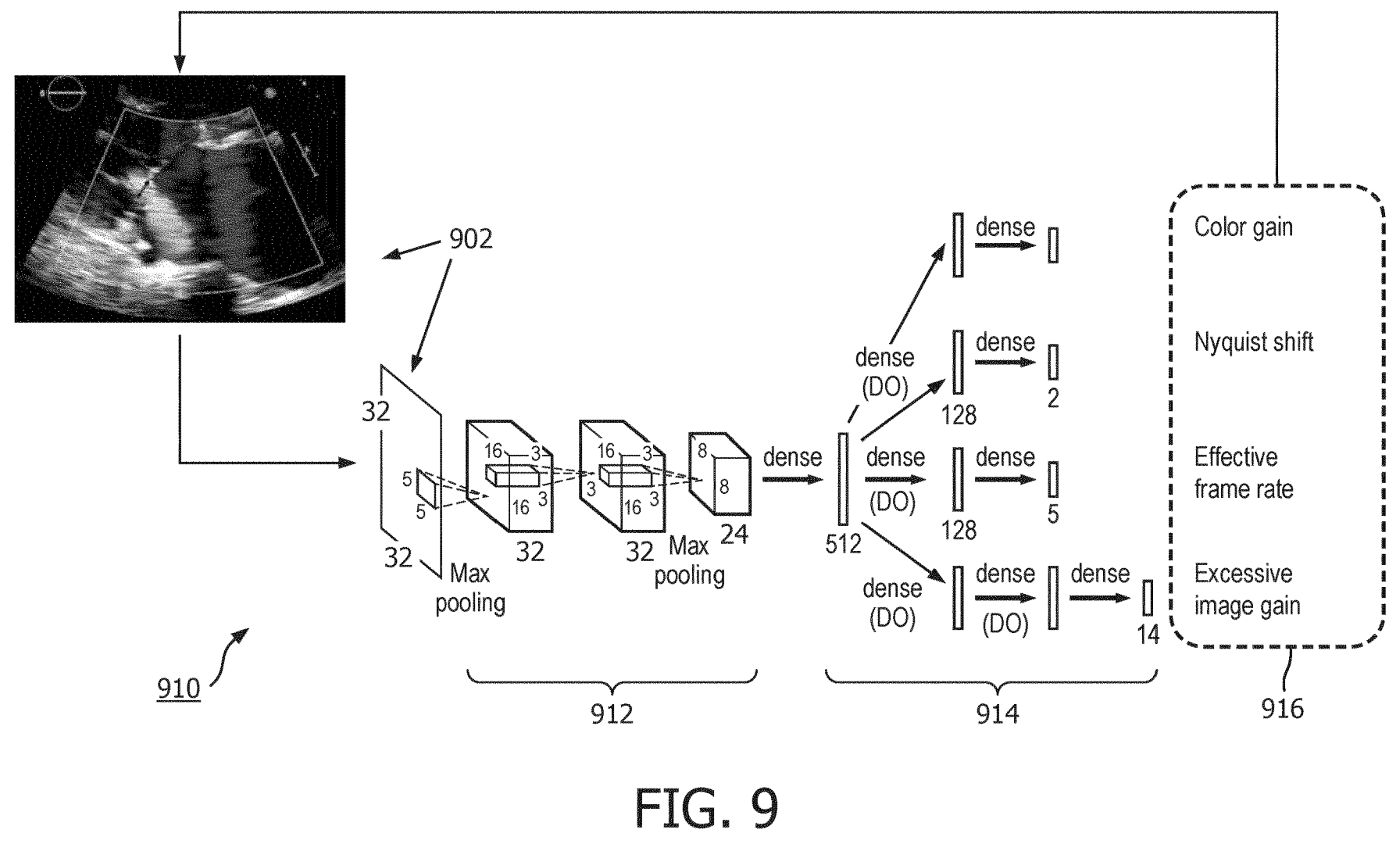

As noted above, given that multiple imaging settings have interplay effects on the jet visualization. In some embodiments, instead of using multiple individually trained models, a multitasking predictive model (e.g., a multi-tasking CNN) may be used to solve for a set of imaging parameters simultaneously. In such examples, a single model may be trained to generate a classification for multiple, in some cases all of the, image settings suitable for obtaining a particular MR measurement. FIG. 9 shows one such example. The predictive model, shown in FIG. 9 as a convolutional neural network 910, receives an input image 902 (e.g., color Doppler image of a target view of the heart) and provides an output vector 906, with each element of the vector representing the classification of a different one of the set of imaging parameters. The classification output may be an indication of the likelihood that the settings produce a quality image, or in some instances, the model is trained to output the optimal settings as the classification output of the network, where the latter may be trained with ground truth including optimized image settings such as settings for the color gain, Nyquist shift, gain, persistence, image gain, etc. In one example, training data inputs for such multi-tasking model may include previously collected Doppler ultrasound images and the ground truth acoustic parameters chosen by the sonographer(s) training the model. The model would thus be trained to output a vector suggesting the optimal setting (e.g., color gain=60, Nyquist shift=60 cm/s, Gain=48 and persistence=None, image gain=52).

Referring to the example in FIG. 9, the network 902 may include any suitable number, type and arrangement of layers, for example a set of N convolutional layers 912, followed by a set of K dense (or fully connected) layers 914, where N and K may be any positive integers. The network 902 generates a multi-parameter output 916, shown here as a vector having a desired number of elements (in this example four) corresponding to the number of imaging settings which the network is trained to simultaneously classify. The multi-parameter output 916 of network 910 for each input image frame may be used, by the processor of the scanner, to generate user guidance when the user has selected manual adjustment mode, or the multi-parameter output of network 910 may be used to iteratively arrive at a set of optimal image settings, also referred to here as optimal MR TSP, which the system then automatically applies to the imaging device for subsequent imaging. For the latter scenario, which is executed when the user has selected auto-TSP mode, the processor automatically and incrementally adjust one or more of the imaging settings based on the prior classification of the settings. For example, one or more of the settings with poor classification may be automatically adjusted, in small increment(s), and a new image frame with the adjusted setting(s) is provided to the network 902, which then outputs a new classification of the set of imaging parameters. In some embodiments, the processor uses pre-programmed logic for the step size and direction of the incremental adjustment of the setting. In some cases, these parameters (e.g., step size) are preprogramed, or they may be defined by a Gauss Newton or other optimization technique. In some embodiments, only a single setting may be adjusted during each iteration, while in other embodiments, multiple ones of the sub-optimal settings may be simultaneously adjusted at each iteration. This process continues, as the user maintains the probe in the appropriate position determined by the earlier steps of the workflow, until the model has classified all settings as acceptable/optimal.

In yet further embodiments, the multitasking network 902 is instead trained to output a vector of the optimal settings, also referred to here as optimal MR TSP. The network 902 may be trained is many sets of color Doppler images and ground truth corresponding to vectors of optimized acoustic parameters, for example chosen by the sonographers (e.g., color gain=56, Nyquist shift=60 cm/s, Gain=44 and persistence=None, image gain=44.). When trained, this network 902 may output a vector of predicted optimal settings when an input image of any given target view is input to the network 902.

Once the processor has arrived at the optimal settings, whether through iterative prediction or by directly predicting the optimal settings, the optimal settings are automatically applied, without user involvement, to the imaging device and optionally a confirmation that the MR TSP has been applied may be provided (e.g., visually or audibly) to the user. The MR exam workflow then moves to the last step(s) of the MR exam involving the collection of the selected measurement.

Referring back to FIG. 6, after tuning the imaging settings, the MR evaluation process continues at block 636 where a sequence of image frames is acquired for at least a predetermined portion of the cardiac cycle. For example, for the VCW measurement, the system either instructs the user to record a cineloop for at least the fully systolic phase, or the system automatically captures this sequence of images and confirms (e.g., with a beep) when sufficient image data has been collected. The processor then identifies the one or more image frames from the just-acquired sequence on which the selected measurement will be based (block 638). For example, for the VCW measurement, the processor selects the frame from the systolic phase sequence that shows the largest VCW. Image segmentation can be used, as previously discussed to identify the components of the jet and thus identify the vena contracta in each frame. The processor then comparatively evaluates the size of the vena contracta from each frame to find the frame with the largest VCW. Once a frame has been selected, the processor can optionally automatically obtain the measurement (block 640) given that the anatomical feature of interest, here the VC, has already been identified in the frame from the previous step. In some cases, and depending upon the level of automation selected by the user, the processor may receive the measurement obtained by the user. In the latter scenario, following the frame selection step, the processor may display the selected frame on the display enabling the user to easily collect the measurement without having to look for or retrieve the desired frame. Once the selected measurement has bene recorded, the processor determines (at block 642) if all predetermined measurements have been obtained and if so, the process 600 terminates. Otherwise, the processor returns to block 610 whereby the user can select the next measurement, or optionally the process automatically continues with the sub-workflow of the next measurement in the sequence.

It will be understood that in some embodiments a combination of the configuration of FIGS. 8A and 9 may be used. That is in some embodiments, a multi-parameter network may be used to generate a subset of all of the image settings and one or more additional individually trained networks may be added for optimization of additional parameters. for example, imaging settings that have greatest amount of interplay may be collectively optimized using a single multitasking network, while settings that do not have as large an interplay with other settings may be individually optimized. In some embodiments, a multitasking network may be used to generate a set of optimal settings that are automatically applied by the system, while one or more individually trained networks provide guidance for manual adjustment to other settings. This latter scenario may be used in embodiments in which the user is able to select a hybrid settings-assist mode which involves some settings being automatically adjusted by the system and some being left to manual adjustment, with visual feedback provided by the system.

FIG. 9 shows a block diagram of a process and elements associated with training and deployment of a predictive model (also referred to as neural network) in accordance with the principles of the present disclosure. The process shown in FIG. 9 may be used to train any one or all of the predicative models that may be employed by the imaging systems described herein, such as models 224 shown in FIG. 2. The left hand side of FIG. 9, phase 1, illustrates the training of a predictive model. To train the predictive model, training data 914, which may include multiple instances of input arrays (e.g., sets of images) and output classifications (e.g., depending on the output parameters desired) may be presented to the training algorithm(s) or engine 910 (e.g., AlexNet training algorithm, as described by Krizhevsky, A., Sutskever, I. and Hinton, G. E. "*ImageNet Classification with Deep Convolutional Neural Networks,*" NIPS 2012 or its descendants). Training may involve the selection of a starting architecture 912 and the preparation of training data 914. The starting architecture 912 may be a blank architecture (e.g., an architecture with defined layers and arrangement of nodes but without any previously trained weights) or a partially trained model, such as the inception networks, which may then be further tailored for classification of ultrasound images. The starting architecture 912 (e.g., blank weights) and training data 914 are provided to a training engine 910 (e.g., ADAM optimizer) for training the model.

Upon sufficient number of iterations (e.g., when the model performs consistently within an acceptable error), the model 920 is said to be trained and ready for deployment, which is illustrated in the middle of FIG. 9, phase 2. The right hand side of FIG. 9, or phase 3, the trained model 920 is applied (via inference engine 930) for analysis of new data 932, which is data that has not been presented to the model during the initial training (in phase 1). For example, the new data 932 may include unknown images such as live ultrasound images acquired during a scan of a patient (e.g., color Doppler images obtained during an MR exam). The trained model 920 implemented via engine 930, which may be executed on the host system (e.g., host 220) is used to classify the unknown images in accordance with the training of the model 920 to provide an output 934 (e.g., generating bounding boxes for image segmentation, generating a classification of direction of the jet and/or of complete visualization including all components and desired direction of the jet, and/or suitability of an image setting for a particular cardiac view for MR quantification). The output 934 of the trained model generated in the field (i.e. applied at the point of care) may then be used by the imaging system for further processes 940 performed by the system, such as generating user guidance and/or automated tuning of the ultrasound scanner for subsequent image data acquisition.

As previously described, in some embodiments, the trained model 920 implements a neural network executed by a processor by a processor of an ultrasound imaging device, and the starting architecture of the model may be that of a convolutional neural network, or a deep convolutional neural network, which may be trained to detect certain anatomical feature (e.g., components of the MR jet or other cardiac structures) and/or to analyze image quality, such as by identifying artefacts or other image features. The training data 914 may include multiple (hundreds, often thousands or even more) annotated/labeled images, also referred to as training images. It will be understood that the training image need not include a full image produced by an imagining system (e.g., representative of the full field of view of the probe acquiring a given cardiac view) but may include patches or portions of images, for example, those portions that include a portion of the cardiac tissue or other regions of interest associated therewith.

In various embodiments, the trained predictive model may be implemented, at least in part, in a computer-readable medium comprising executable instructions executed by a processor, e.g., image processor 236. The trained model or aspects thereof such as the weights between interconnected neurons of the network and/or biases, as tuned during the training process, may be stored locally on the ultrasound system or may be remotely located (e.g., on a networked storage device) and accessed via a suitable (e.g., wired or wireless) communication link between the ultrasound device and the remote storage device.

Figure 11:
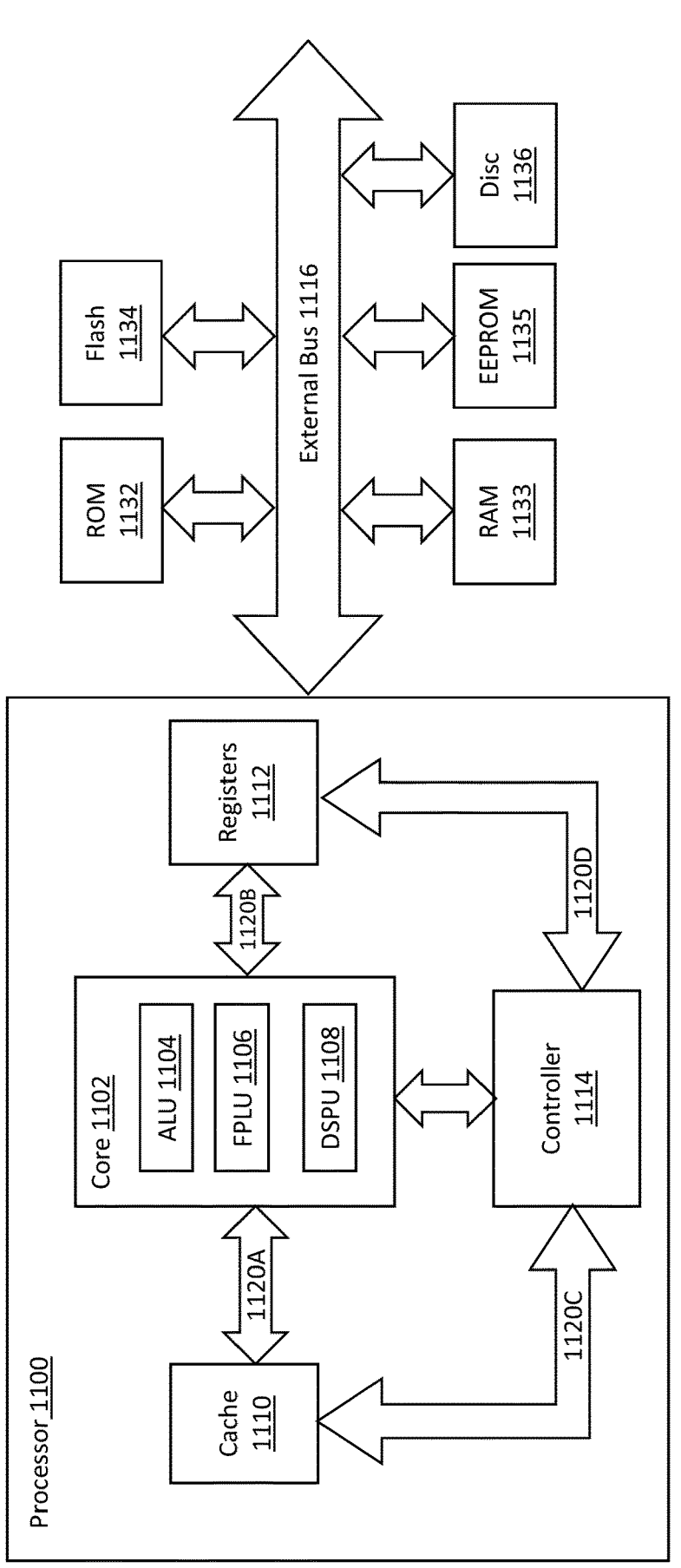
FIG. 11 is a block diagram of an example processor in accordance with the principles of the present disclosure.

In some examples, to obtain ground truth, such as for detecting fully visualized MR jet and/or otherwise properly visualized target view, trained sonographers may annotate ultrasound images, which may include B-mode or color Doppler images or sequences thereof by placing bounding boxes around the anatomical feature or flow feature to be detected by the model. In some embodiments, the generating of ground truth images may be assisted by segmentation methods. For example, segmenting flow in color Doppler images may be achieved with known segmentation technique to simply segment the portion of the image on which flow is identified via the color overlay. Thus, annotation for preparing training data may include a combination of computer-based segmentation and sonographer verification and/or labeling of the image. In some embodiments, reinforcement learning may be used where a reward function based on the quality of the acquired image is used. As the reinforcement learning progresses, the system (e.g., the machine learning model) learns to maximize the reward, thus learning to output images with higher quality. Different learning approaches may be combined, for example combining a model that classifies images and which also maximizes a reward function, such as one based on quality of the image. Furthermore, a trained model may continue to be fine-tuned after deployment (at phase 3), as shown in FIG. 9, such as through field training 938 that uses images obtained during field use of the trained model. FIG. 11 is a block diagram illustrating an example processor 1100 according to principles of the present disclosure. Processor 1100 may be used to implement one or more processors and/or controllers described herein, for example, image processor 236 shown in FIG. 2 and/or any other processor or controller shown in FIG. 2. Processor 1100 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 1100 may include one or more cores 1102. The core 1102 may include one or more arithmetic logic units (ALU) 1104. In some embodiments, the core 1102 may include a floating point logic unit (FPLU) 1106 and/or a digital signal processing unit (DSPU) 1108 in addition to or instead of the ALU 1104.

The processor 1100 may include one or more registers 1112 communicatively coupled to the core 1102. The registers 1112 may be implemented using dedicated logic gate circuits (e.g., flip-flops) and/or any memory technology. In some embodiments the registers 1112 may be implemented using static memory. The register may provide data, instructions and addresses to the core 1102.

In some embodiments, processor 1100 may include one or more levels of cache memory 1110 communicatively coupled to the core 1102. The cache memory 1110 may provide computer-readable instructions to the core 1102 for execution. The cache memory 1110 may provide data for processing by the core 1102. In some embodiments, the computer-readable instructions may have been provided to the cache memory 1110 by a local memory, for example, local memory attached to the external bus 1116. The cache memory 1110 may be implemented with any suitable cache memory type, for example, metal-oxide semiconductor (MOS) memory such as static random access memory (SRAM), dynamic random access memory (DRAM), and/or any other suitable memory technology.

The processor 1100 may include a controller 1114, which may control input to the processor 1100 from other processors and/or components included in a system (e.g., control panel 252 and scan converter 230 shown in FIG. 2) and/or outputs from the processor 1100 to other processors and/or components included in the system (e.g., display 238 and volume renderer 234 shown in FIG. 2). Controller 1114 may control the data paths in the ALU 1104, FPLU 1106 and/or DSPU 1108. Controller 1114 may be implemented as one or more state machines, data paths and/or dedicated control logic. The gates of controller 1114 may be implemented as standalone gates, FPGA, ASIC or any other suitable technology.

The registers 1112 and the cache memory 1110 may communicate with controller 1114 and core 1102 via internal connections 1120A, 1120B, 1120C and 1120D. Internal connections may implemented as a bus, multiplexor, crossbar switch, and/or any other suitable connection technology.

Inputs and outputs for the processor 1100 may be provided via a bus 1116, which may include one or more conductive lines. The bus 1116 may be communicatively coupled to one or more components of processor 1100, for example the controller 1114, cache memory 1110, and/or register 1112. The bus 1116 may be coupled to one or more components of the system, such as display 238 and control panel 252 mentioned previously.

The bus 1116 may be coupled to one or more external memories. The external memories may include Read Only Memory (ROM) 1132. ROM 1132 may be a masked ROM. Electronically Programmable Read Only Memory (EPROM) or any other suitable technology. The external memory may include Random Access Memory (RAM) 1133. RAM 1133 may be a static RAM, battery backed up static RAM. Dynamic RAM (DRAM) or any other suitable technology. The external memory may include Electrically Erasable Programmable Read Only Memory (EEPROM) 1135. The external memory may include Flash memory 1134. The external memory may include a magnetic storage device such as disc 1136. In some embodiments, the external memories may be included in a system, such as ultrasound imaging system 200 shown in FIG. 2, for example local memory 242.

Although the examples described herein discuss processing of ultrasound image data, it is understood that the principles of the present disclosure are not limited to ultrasound and may be applied to image data from other modalities such as magnetic resonance imaging and computed tomography.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system for quantifying mitral regurgitation of a heart of a subject, the system comprising:
   an ultrasound imaging device including a probe configured to transmit ultrasound into the subject in accordance with acquisition settings and to receive ultrasound echoes for generating ultrasound images of the heart;
   a display configured to display one or more of the ultrasound images; and
   a processor in communication with the ultrasound imaging device and the display, wherein the processor is configured to:
   receive one or more ultrasound images of the heart that show a mitral regurgitation (MR) jet;
   provide a graphical user interface (GUI) for an MR exam, wherein the GUI is configured to enable a user to make a selection of an automation setting and a measurement from a plurality of predetermined measurements consisting of vena contracta width (VCW), regurgitant volume (RVol), regurgitant fraction (RF) and effective regurgitant orifice area (EROA);
   receive a user input via the GUI, wherein the user input comprises the selected automation setting and the selected measurement; and
   for one or more of the selected measurements of the plurality of measurements, and based on the one or more images, provide measurement-specific user guidance on the display for at least one of positioning the probe, adjusting acquisition settings, and determining a target frame from a sequence of ultrasound images of the MR jet for obtaining the selected measurement.

2. The system of claim 1, wherein the processor is configured to determine whether the one or more ultrasound images show a target cardiac view, wherein the target cardiac view depends on the selected measurement, and to provide guidance to the user for positioning the probe with respect to the subject to acquire the target cardiac view.

3. The system of claim 2, wherein the processor is configured, responsive to selection of the RVol or RF, to:

determine whether the one or more ultrasound images show apical 4-chamber (A4C) view; and upon determining that the one or more ultrasound images do not show a A4C view, provide user guidance for positioning the probe to acquire the A4C view.

4. The system of claim 1, wherein the selection of the automation setting comprises selecting an automated tissue specific preset (auto-TSP) mode, and wherein the processor is configured to:

automatically adjust the acquisition settings to processor-estimated MR-specific TSP settings if the auto-TSP mode is selected; and provide guidance on the display for manually adjusting acquisition settings if the auto-TSP mode is not selected.

5. The system of claim 4, wherein the processor is configured to estimate the MR-specific TSP settings using a predictive model trained to generate a multi-parameter output comprising a set of estimated optimal values for each of a plurality of acquisition settings selected from color gain, Nyquist shift, frame rate and image gain.

6. The system of claim 4, wherein the processor is configured to use at least one predictive model to classify at least one acquisition setting associated with the image, wherein the classification indicates suitability of the at least one acquisition setting for MR evaluation, the processor being further configured to display a visual indicator of the suitability concurrently with the image.

7. The system of claim 1, wherein the processor is further configured to automatically obtain the selected measurements from the determined target frame.

8. The system of claim 1, wherein the processor is configured, responsive to selection of the VCW, to:

a direction of the MR jet from the one or more ultrasound images;

provide user guidance for adjusting the probe to a position in which the probe is substantially parallel to the direction of the MR jet;

acquire the sequence of ultrasound images spanning at least one full phase of a cardiac cycle of the heart; and the target frame for measuring the VCW from the sequence of ultrasound images spanning at least one full phase of a cardiac cycle of the heart.

9. The system of claim 8, wherein the processor is configured, prior to determining the direction of the MR jet, to:

whether the one or more ultrasound images show a parasternal long-axis view; and upon determining that the one or more ultrasound images do not show a PLAX view, provide user guidance for positioning the probe to acquire the PLAX view.

10. The system of claim 9, wherein the processor is configured to provide the one or more ultrasound images to a predictive model trained to identify components of the MR jet from ultrasound images, and wherein the processor determines the direction of the MR jet based on the components of the MR jet identified by the deep learning model.

11. The system of claim 10, wherein the processor is configured, when providing user guidance for adjusting the probe, to compare an azimuthal direction of the probe to the direction of the MR jet, and provide a visual indicator of alignment of the probe to the direction of the MR jet.

12. The system of claim 1, wherein the processor uses one or more predictive models to provide the measurement-specific user guidance on the display.

13. The system of claim 12, wherein the one or more predictive models include a first model configured to identify components of the MR jet in images input to the first model, at least one second predictive model configured to classify one or more imaging settings of the input image.

14. The system of claim 13, wherein the at least one second predictive model comprises a trained neural network configured to provide a multi-parameter output comprising a classification for a plurality of image settings as a set, wherein the classification indicates either a quality of each of the image settings or an estimated optimal value for each image setting.

15. The system of claim 14, wherein the trained neural network is configured to output, for each input image, a classification for each of color gain, Nyquist shift, frame rate and image gain.

* * * * *